Figure 1:
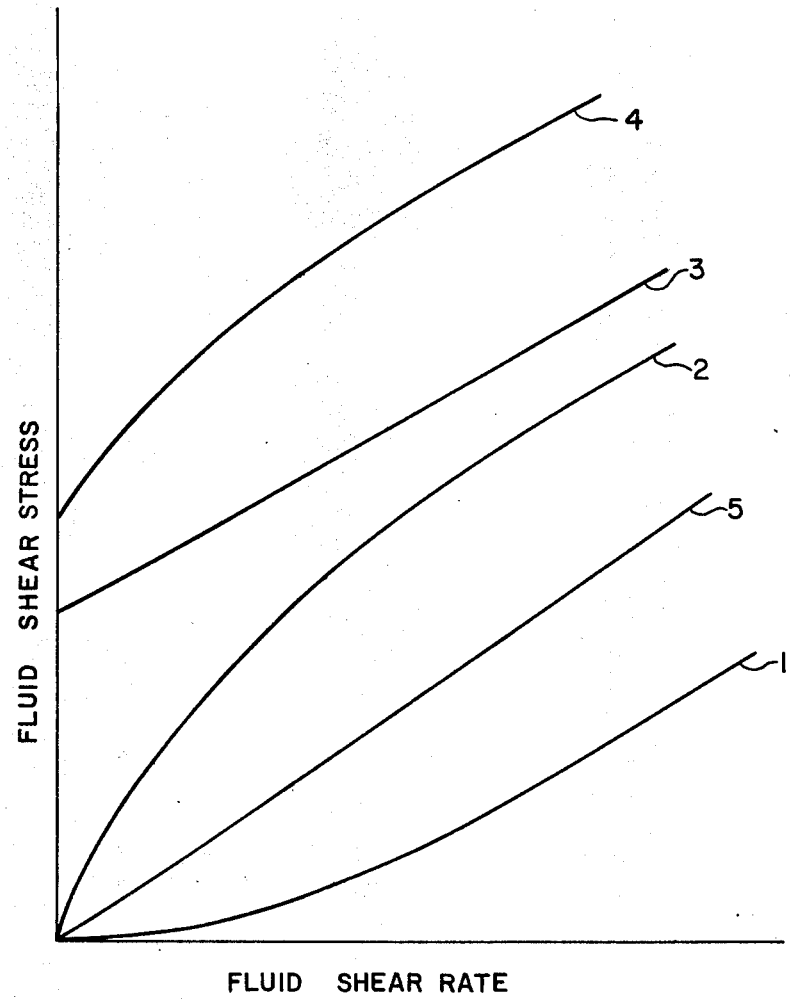

United States Patent [19]

Hayes et al.

[11] 3,952,577

[45] Apr. 27, 1976

[54] APPARATUS FOR MEASURING THE FLOW RATE AND/OR VISCOUS CHARACTERISTICS OF FLUIDS

[75] Inventors: William F. Hayes; John W. Tanney, both of Ottawa; Helen G. Tucker, Orleans, all of Canada

[73] Assignee: Canadian Patents and Development Limited, Ottawa, Canada

[22] Filed: Feb. 6, 1975

[21] Appl. No.: 547,607

[30] Foreign Application Priority Data
Mar. 22, 1974 Canada ................................ 195776

[52] U.S. Cl. .................................. 73/55; 73/205 R; 73/212
[51] Int. Cl.² ....................... G01F 1/46; G01F 1/48; G01N 11/08
[58] Field of Search ................ 73/55, 56, 205, 212

[56] References Cited
UNITED STATES PATENTS

| | | | |
|---|---|---|---|
| 1,586,948 | 6/1926 | Connet | 73/205 |
| 1,963,011 | 6/1934 | Albersheim et al. | 73/205 X |
| 2,503,676 | 4/1950 | Marusov | 73/205 |
| 2,700,891 | 2/1955 | Shafer | 73/55 |
| 3,677,069 | 7/1972 | Rubin et al. | 73/56 |

FOREIGN PATENTS OR APPLICATIONS

| | | | |
|---|---|---|---|
| 123,771 | 1/1959 | U.S.S.R. | 73/205 |

*Primary Examiner*—Herbert Goldstein
*Attorney, Agent, or Firm*—Francis W. Lemon

[57] ABSTRACT

An apparatus for measuring the flow rate and/or viscous characteristics of a fluid comprising a casing having a fluid passage, a fluid inlet cavity and a fluid outlet cavity, fluid pressure detecting means preferably at spaced positions along the passage, and fluid pressure indicating means for indicating the or each characteristic to be measured in terms of the fluid pressure differential between the detecting means positions. The fluid inlet cavity provides a substantially unobstructed flow path to the fluid passage and the fluid outlet cavity provides a substantially unobstructed flow path therefrom. The fluid passage cross-sectional area decreases in the fluid flow direction in order to maintain laminar flow of the fluid therealong and wall boundary induced viscous shear therealong, over an extended range of Reynolds number within the fluid passage and formulae are given, using substantially pure water as a standard fluid, from which the limits of fluid passage geometry can be defined. In one embodiment the fluid passage is annular in shape and the fluid flow radially inward. The fluid passage may be divided into a plurality of substantially identical fluid passages to increase the flow rate capacity of the apparatus.

38 Claims, 24 Drawing Figures

APPARATUS FOR MEASURING THE FLOW RATE AND/OR VISCOUS CHARACTERISTICS OF FLUIDS

This invention relates to an apparatus for measuring the flow rate and/or the viscous characteristics of fluids.

In this specification viscous characteristics of a fluid are considered to be the absolute viscosity of a Newtonian fluid, or the shear stress/shear rate characteristics of a non-Newtonian fluid.

Further, in this specification Newtonian fluids are defined as those exhibiting a direct proportionality between shear stress and shear rate in laminar flow at a fixed temperature and pressure, while non-Newtonian fluids are defined as those exhibiting non-linear shear stress dependency upon shear rate, and/or a finite shear stress at zero shear rate (i.e., a fluid exhibiting a yield stress), in laminar flow at a fixed temperature and pressure.

Further, in this specification, a fluid may consist of a gas, a liquid, a combination of gas and liquid, gas and suspended solid, liquid and suspended solids, or a combination of gas, liquid and suspended solids.

The measurements of fluid flow rate and fluid viscosity are long standing problems which have been approached with a wide variety of techniques, each of which exhibits particular advantages and deficiencies relative to particular applications.

The principles relative by measuring fluid flow rates may be classified into five general groupings:

Heat transfer rate to or from fluids as exemplified by hot wire anemometers or similar devices.

Transport time of extraneous media suspended in or driven by the fluid as exemplified by the time displacement relationship of ion clouds, solid bodies, bubbles, etc; transport time of disturbances within the fluid itself as exemplified by the time displacement correlation of inherent or induced fluid turbulence noise spectra.

Fluid momentum detection as exemplified by pitot tubes or venturi meters; fluid momentum utilization as exemplified by cup anemometers or tubine meters; and fluid momentum interaction as exemplified by fluid jet velocity sensors.

Fluid disturbance detection as exemplified by vortex shedding flowmeters and vortex generation detecting swirlmeters.

Fluid viscosity induced phenomena as exemplified by laminar flow pressure drop devices.

Many types of apparatus are available for measuring the viscosity of fluids (Reference, Viscosity and Flow Measurement — A Laboratory Handbook of Rheology; Van Wazer, Lyons, Kim, Colwell; Interscience, N.Y., 1963), but most give only a qualitative indication of viscosity in that the fluid shear stress and shear rate cannot be measured simultaneously at a given point within the apparatus. Many such apparatus have outputs which are complex functions of fluid properties in addition to viscosity and as such must be used with discretion.

Known types of apparatus presently used for the precise measurement of fluid viscosity may be classified into three general groupings:

capillary-tube viscometer where the fluid viscosity is directly related to the frictional pressure drop and laminar flow rate through a long smooth tube rotary viscometer where the fluid is sheared within an annulus between two concentric cylinders, one of which is rotating, the fluid viscosity being directly related to the reaction torque and speed of the cylinders.

falling-sphere viscometer where the fluid viscosity is directly related to the velocity of a sphere free-falling through the fluid as dependent upon the sphere frictional drag.

These known types of apparatus suffer from the disadvantage that they are not suitable in their basic configurations for measuring a wide range of flow rates nor are they suitable in their basic configurations of continuously measuring the viscosity of a flowing fluid.

It is an object of the present invention to provide an apparatus capable of measuring a wide range of flow rates and/or viscosity characteristics of an extensive variety of fluids such that the output pressure differential of the said apparatus can be continuously related to the said fluid characteristics in a consistent and deducible manner in contrast with the stated disadvantages of the known types of apparatus for measuring fluid flow rate and/or viscosity.

According to the present invention there is provided an apparatus for measuring the flow rate and/or the viscous characteristics of a fluid, comprising:

a. a casing having a fluid passage, a fluid inlet cavity for connection to a source of pressurized fluid and forming a substantially unobstructed flow path for fluid to the whole area of an inlet end of the fluid passage, normal to the direction for flow of fluid in the fluid passage, and a fluid outlet cavity for the escape of fluid from the casing and forming a substantially unobstructed flow path for fluid from substantially the whole area of an outlet end of the fluid passage, normal to the direction for flow of fluid in the fluid passage, b. fluid pressure detecting means in the casing for detecting a fluid pressure differential between spaced positions in the fluid passage in the direction for flow of fluid therein, and c. fluid pressure indicating means, connected to the fluid pressure detecting means from which the fluid pressure differential in the fluid passage can be deduced, and wherein, d. the ratio of the mean breadth to the mean width of the fluid passage area, normal to the direction for flow of fluid therein, is at least ten to one for at least the portion of the fluid passage which extends between the said spaced positions, e. the area of the fluid passage, normal to the direction for flow of fluid in the fluid passage, and for at least the portion of the fluid passage which extends between the said spaced positions, continuously reduces in size in the direction for flow of the fluid such that laminar fluid flow will be maintained in the passage, and such that when using substantially pure water at 70°F as a standard, i. if the fluid pressure detecting means detects a static pressure differential, the static pressure differential $\Delta p$ thereof detected by the fluid pressure detecting means is dependant upon the mass flow rate G of the substantially pure water through the fluid passage and satisfies the relationship in consistent units:

$$\Delta p = K_1 (G)^2 + K_2 (G), \text{ and}$$

ii. if the fluid pressure detecting means detects a total pressure differential, the total pressure differential $\Delta P$ thereof detected by the fluid pressure detecting means is linearly dependant upon the mass flow rate G of the substantially pure water in the fluid passage, and the pressure differential for static and total pressure differential detection ($\Delta p$ and $\Delta P$ respectively) whichever is used, is determined over a range of flow rates for the substantially pure water for which the difference between the maximum Reynolds numbers in the fluid passage between the said spaced positions therein is within the range 0 and 8000, where the Reynolds number $R_e$ is defined, in consistent units, by:

$R_r = h\rho U/\mu$, where $h$ = the mean width of the fluid passage at the position between the said spaced positions for which the Reynolds number is a maximum, $\rho$ = the fluid density of the substantially pure water, $U$ = the mean velocity of the substantially pure water at the position between the said spaced positions for which the Reynolds number is a maximum, and $\mu$ = the absolute viscosity of the substantially pure water, and where in the case of static pressure differential detection means the ratio $K_1/K_2$ is greater than 0.01, where $K_1$ and $K_2$ are constants for a given fluid passage geometry and are determined from the relationships $$K_2 = \frac{\Delta P_1 - \Delta P_2 \left(\frac{G_1^2}{G_2^2}\right)}{G_1 - \frac{(G_1^2)}{G_2}},$$

and $$K_1 = \frac{\Delta P_1 - K_2(G_1)}{(G_1)^2} = \frac{\Delta P_2 - K_2(G_2)}{(G_2)^2},$$

where $\Delta p_1$ = static pressure differential between the said spaced positions when the maximum Reynolds number in the fluid passage between the said spaced positions is 8000, $G_1$ = the fluid mass flow rate of the substantially pure water through the fluid passage when the maximum Reynolds number in the fluid passage between the said spaced positions is 8000, $\Delta p_2$ = static pressure differential between the said spaced positions when the maximum Reynolds number in the fluid passage between the said spaced positions is 3500, $G_2$ = the fluid mass flow rate of the substantially pure water through the fluid passage when the maximum Reynolds number in the fluid passage between the said spaced positions is 3500, so that f. the fluid characteristic to be measured is related to the pressure differential indicated by the fluid pressure differential indicating means, and is deducible therefrom in a consistent manner for different fluids.

Further according to the present invention there is provided an apparatus for measuring the flow rate and/or the viscous characteristics of a fluid, comprising:

a. a casing having a plurality of substantially identical fluid passages, a fluid inlet cavity for connection to a source of pressurized fluid and forming a substantially unobstructed flow path for fluid to the whole area of the inlet end of each fluid passage, normal to the direction for flow of fluid in the fluid passage, and a fluid outlet cavity forming a substantially unobstructed flow path for the escape of fluid from the whole area of the outlet end of each fluid passage, normal to the direction for flow of fluid in the fluid passage, b. fluid pressure detecting means in the casing for detecting a fluid pressure differential between spaced positions in at least one of the fluid passages in the direction for flow of fluid therein, and c. fluid pressure indicating means, connected to the fluid pressure detecting means, from which the fluid pressure differential in at least the said one of the fluid passages can be deduced, and wherein, d. the ratio of the mean breadth to the mean width of each fluid passage area, normal to the direction for flow of fluid therein, is at least ten to one for at least the portion of the fluid passages which extends between the said spaced positions, e. the area of each fluid passage, normal to the direction for flow of fluid in the fluid passage, and for at least the same portion of each fluid passage as that which extends between the said spaced positions, continuously reduces in size in the direction for flow of the fluid such that laminar fluid flow will be maintained in each fluid passage, and each fluid passage is such that when using substantially pure water at 70°F as a standard, and i. if the fluid pressure detecting means detects a static pressure differential, the static pressure differential $\Delta p$ thereof detected by the fluid pressure detecting means is dependant upon the mass flow rate G of the substantially pure water through the fluid passage and satisfies the relationship in consistent units:

$\Delta p = K_1(G)^2 + K_2(G)$,
and ii. if the fluid pressure detecting means detects a total pressure differential, the total pressure differential $\Delta P$ thereof detected by the fluid pressure detecting means is linearly dependant upon the mass flow rate G of the substantially pure water in the fluid passage, and the pressure differential for static and total pressure differential detection ($\Delta p$ and $\Delta P$ respectively), whichever is used, is determined over a range of flow rates for the substantially pure water for which the difference between the maximum Reynolds numbers in the fluid passage between the said spaced positions therein is within the range 0 and 8000, where the Reynolds number $R_e$ is defined, in consistent units, by:

$R_r = h\rho U/\mu$, where $h$ = the mean width of the fluid passage at the position between the said spaced positions for which the Reynolds number is a maximum, $\rho$ = the fluid density of the substantially pure water, $U$ = the mean velocity of the substantially pure water at the position between the said spaced positions for which the Reynolds number is a maximum, $\mu$ = the absolute viscosity of the substantially pure water, and where in the case of static pressure differential detection means the ratio $K_1/K_2$ is greater than 0.01, and $K_1$ and $K_2$ are constants for given substantially identical fluid passage geometries and are determined from the relationships:

$$K_2 = \frac{\Delta P_1 - P_2 \left(\frac{G_1{}^2}{G_2}\right)}{G_1 - \frac{(G_1)^2}{G_2}},$$

and $$K_1 = \frac{\Delta P_1 - K_2(G_1)}{(G_1)^2} \quad \frac{\Delta P_2 - K_2(G_2)}{(G_2)^2},$$

where $\Delta p1$ = static pressure differential between the said spaced positions when the maximum Reynolds number in the fluid passage between the said spaced positions is 8000, $G_1$ = the fluid mass flow rate of the substantially pure water through the fluid passage when the maximum Reynolds number in the fluid passage between the said spaced positions is 8000, $\Delta p2$ = static pressure differential between the said spaced positions when the maximum Reynolds number in the fluid passage between the said spaced positions is 3500, $G_2$ = the fluid mass flow rate of the substantially pure water through the fluid passage when the maximum Reynolds number in the fluid passage between the said spaced positions is 3500, so that f. the characteristic to be measured is related to the pressure differential, indicated by the fluid pressure differential indicating means, and is deducible therefrom in a consistent manner for different fluids.

It will be appreciated by those skilled in the art that it is only necessary to determine either the static pressure differential $\Delta p$ or total pressure differential $\Delta P$ in order to numerically evaluate whether any selected passage geometry meets the limiting criteria as per the provisions of i) or ii) of e) above because any selected fluid passage geometry which has been numerically evaluated by a static pressure differential to meet the limiting criteria as per the provision i) would, if so tested, meet the limiting criteria for a total pressure differential as per the provision ii) and vice versa.

Once a particular fluid passage geometry has been numerically evaluated by a static pressure differential or total pressure differential to meet the limiting criteria as per provisions i) or ii) of e) above it will be appreciated that it is not necessary to numerically evaluate any other apparatus in this manner having substantially the same fluid passage geometry. Thus any apparatus having substantially the same fluid passage geometry may have fluid pressure detecting means provided solely for the purpose of providing a pressure differential from which the fluid characteristic to be measured may be deduced.

The apparatus according to the present invention ensures that:

i. laminar flow is maintained in the fluid passage between the detectors over the large Reynolds number range for the fluid flowing therethrough by means of the reduction, in the flow direction, of the passage cross-sectional area normal to the flow direction ii). a pressure differential is generated between the two detector locations by means of wall boundary layer induced viscous shear energy dissipation in the fluid passage.

In this specification, laminar flow is differentiated from turbulent flow by the absence of significant random or irregular flow velocity components.

Additionally in this specification, a pressure detection means in communication with a spaced position shall be interpreted to mean that a pressure detector is located within the apparatus such that pressure variations sensed by the said detector are substantially identical to pressure variations at the said spaced position for a specified operational mode of the apparatus.

Figure 2:
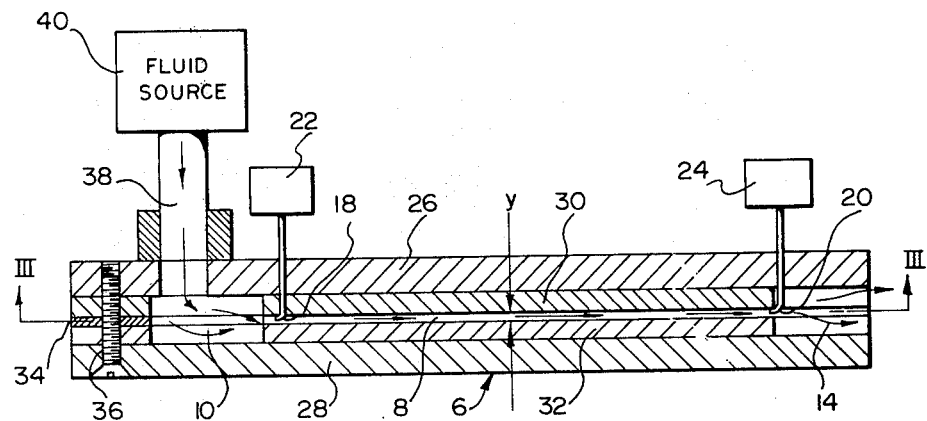
Figure 3:
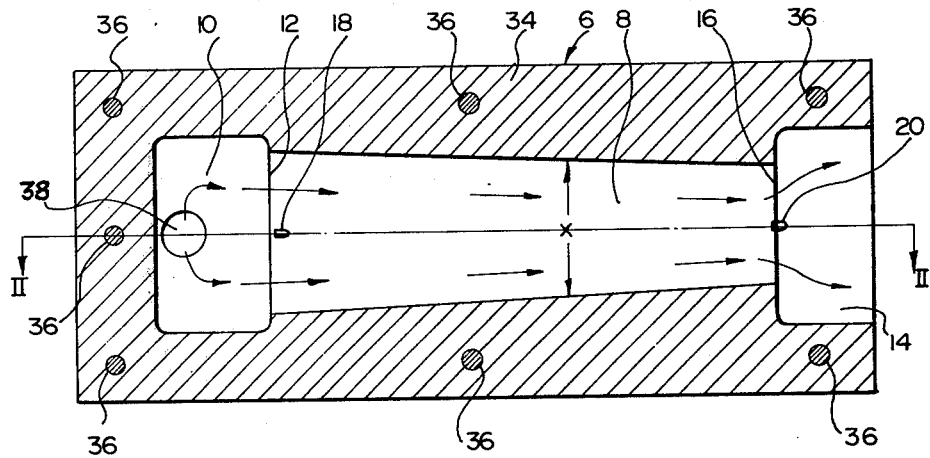
Figure 4:
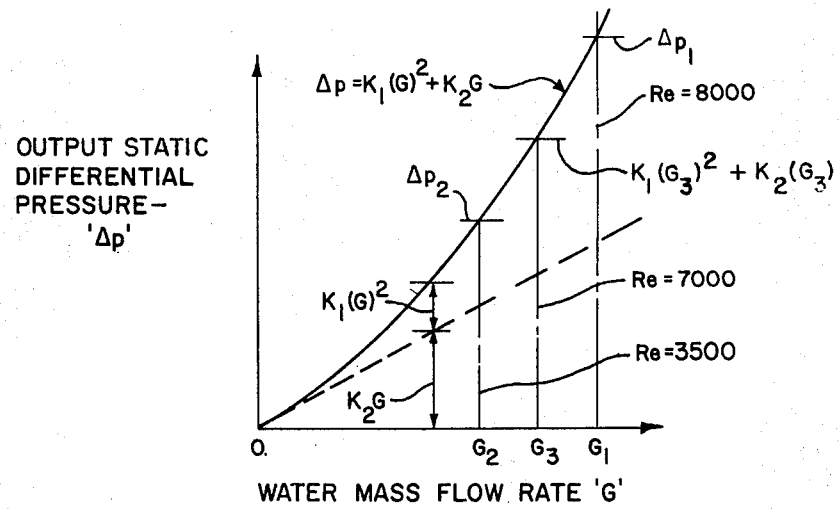
Figure 5:
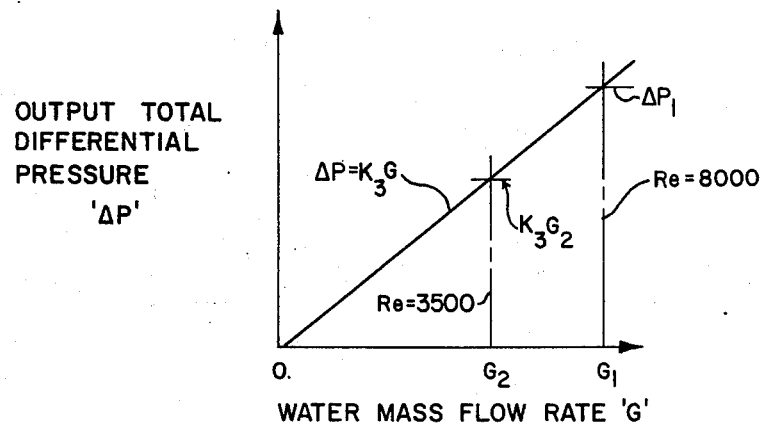
Figure 6:
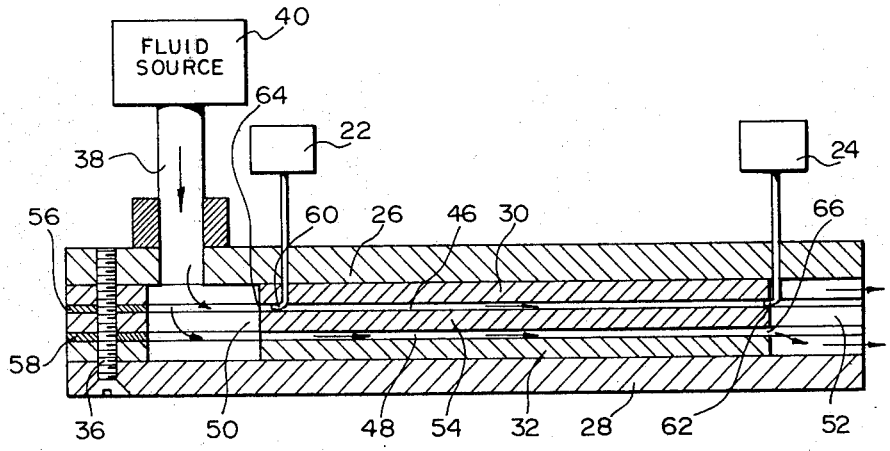
Figure 7:
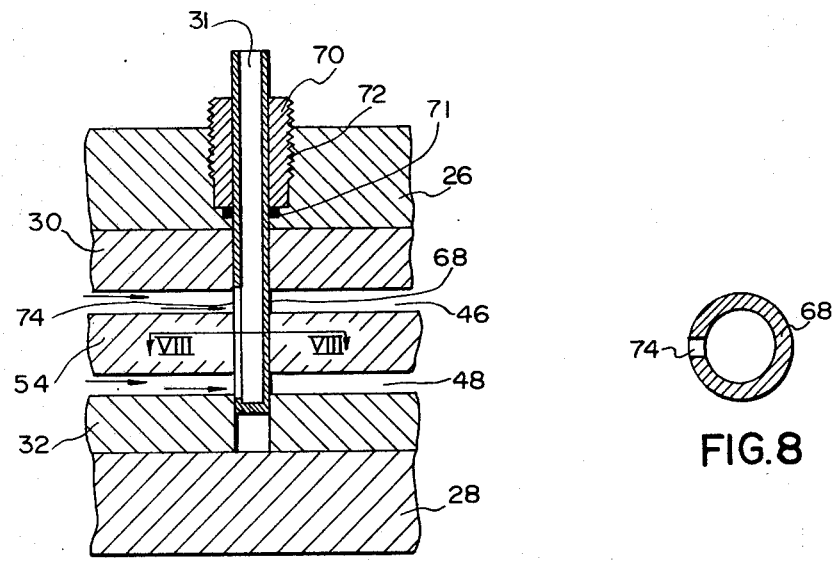
Figure 8:
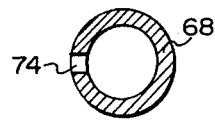
Figure 9:
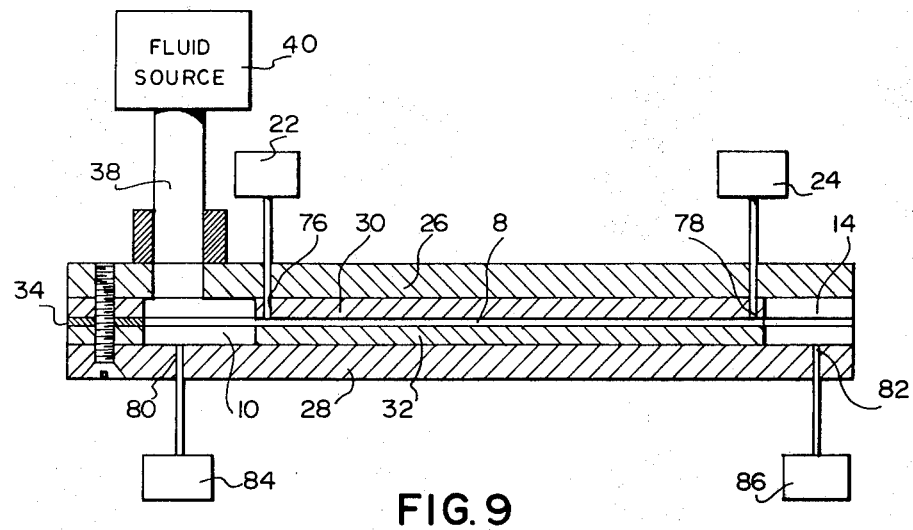
Figure 10:
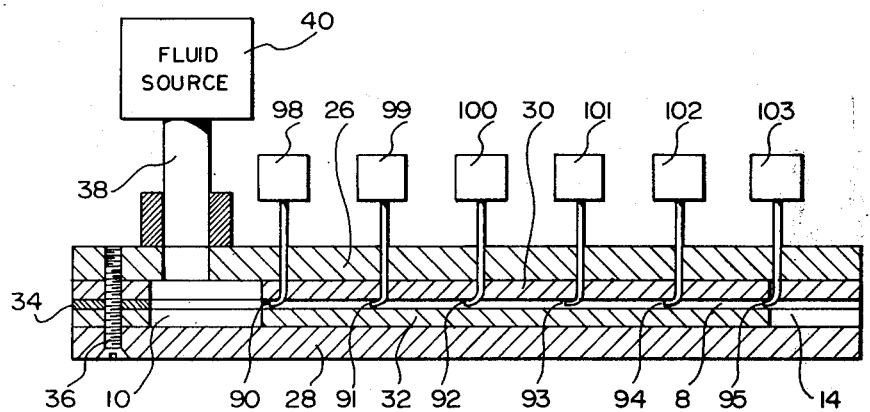
Figure 11:
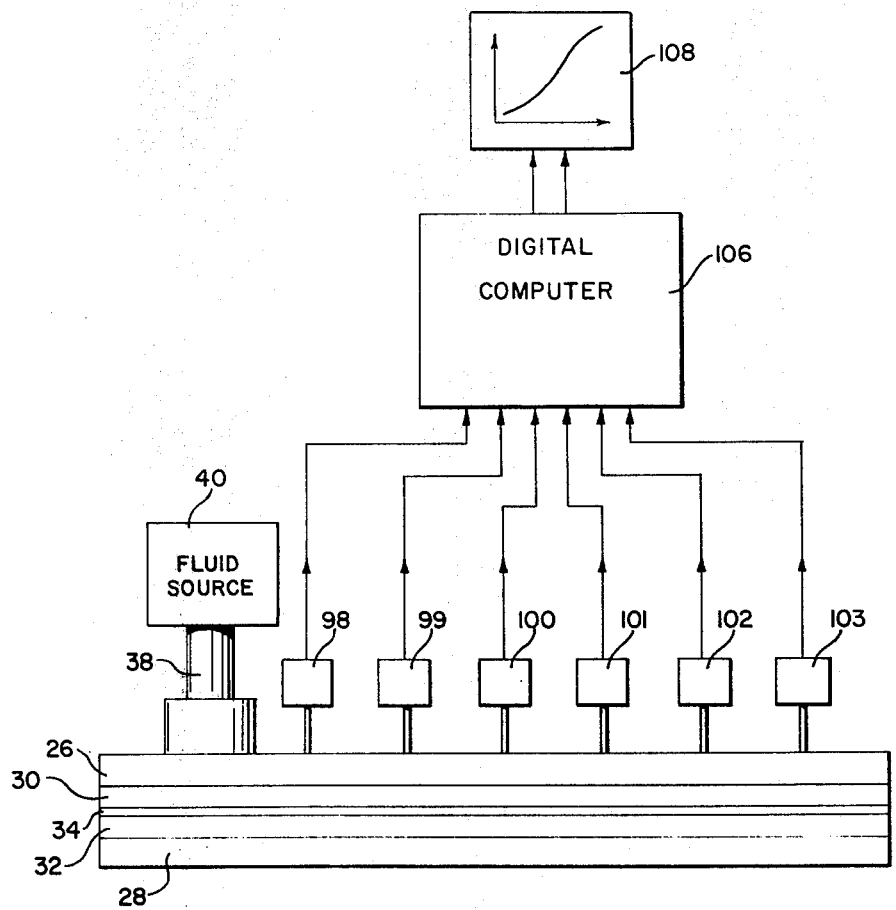
Figure 12:
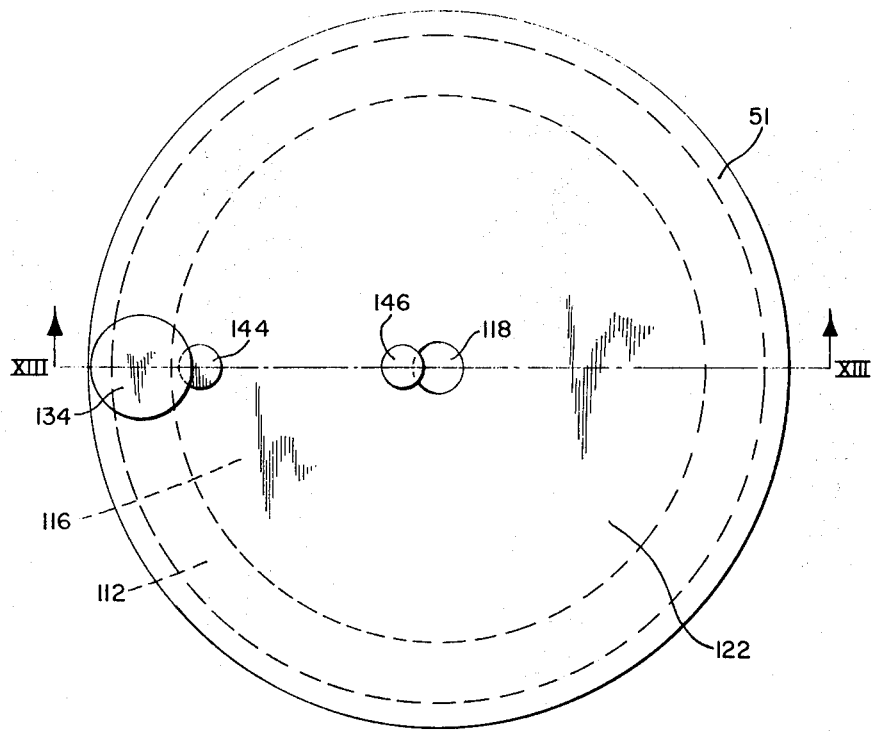
Figure 13:
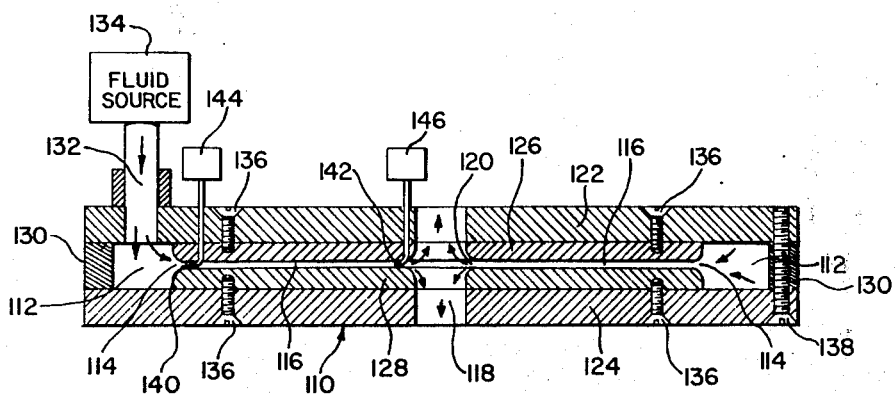
Figure 14:
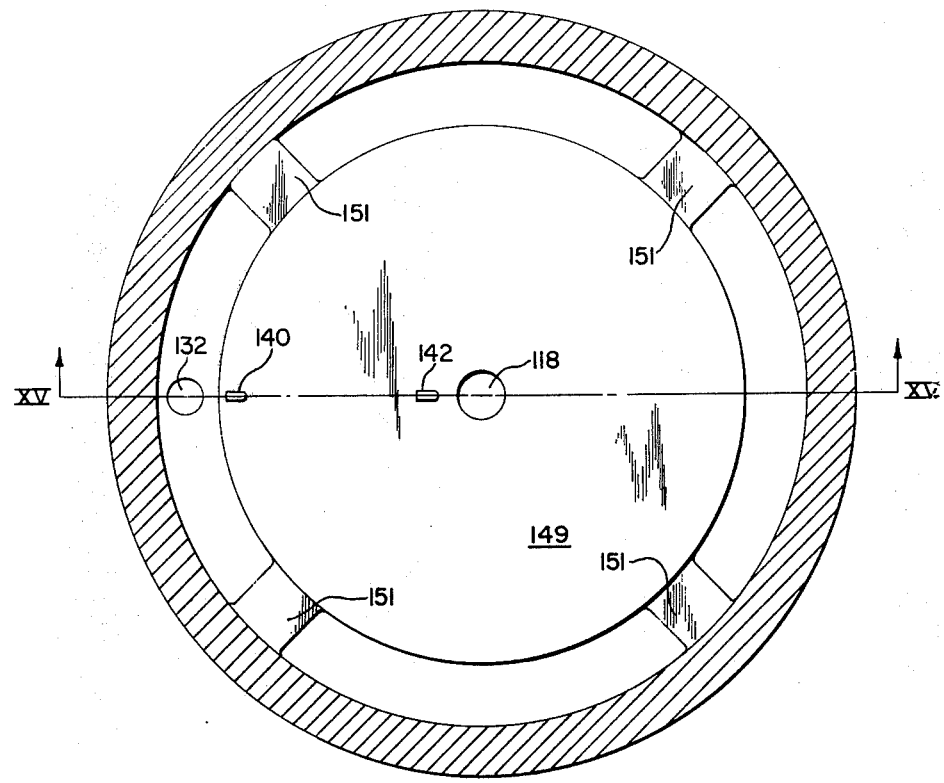
Figure 15:
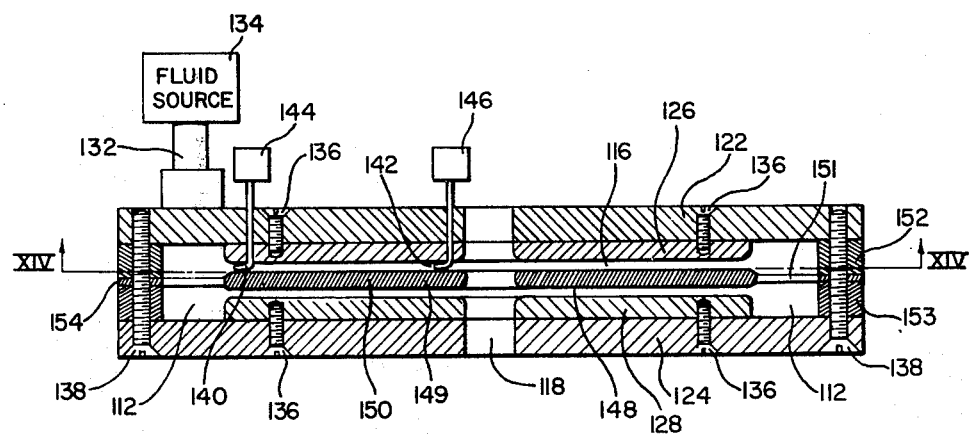
Figure 16:
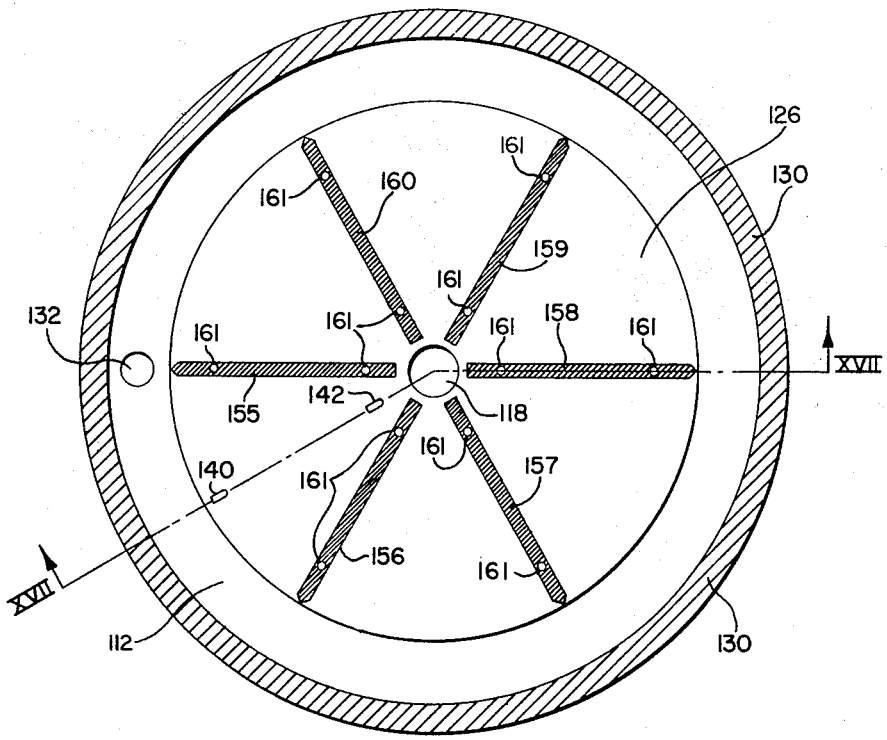
Figure 17:
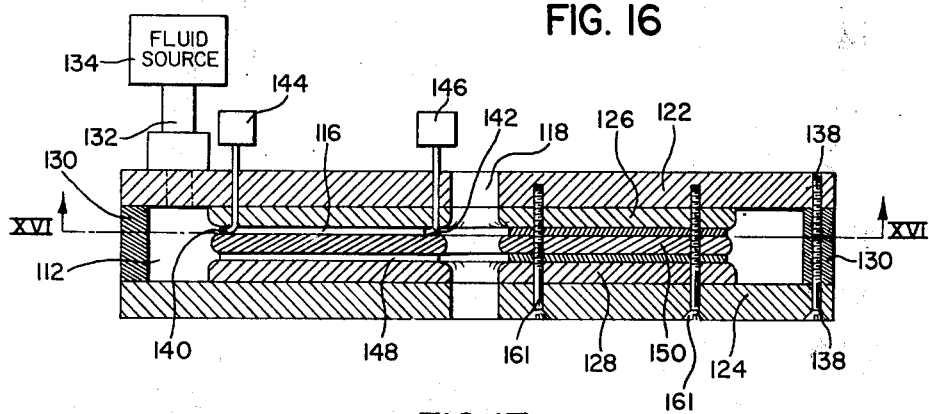
Figure 18:
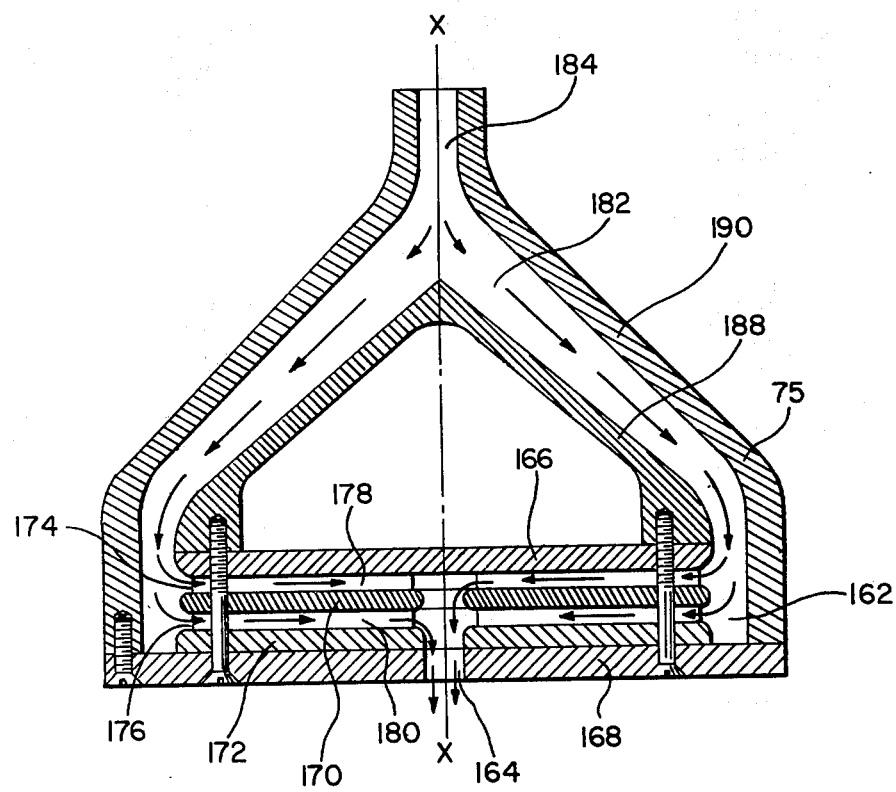
Figure 19:
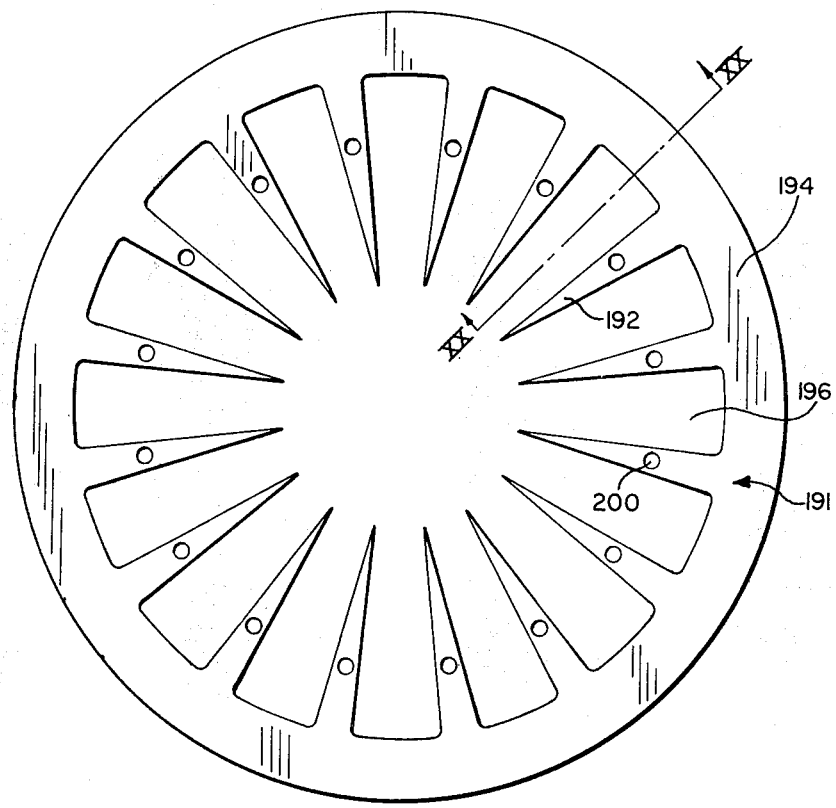
Figure 20:
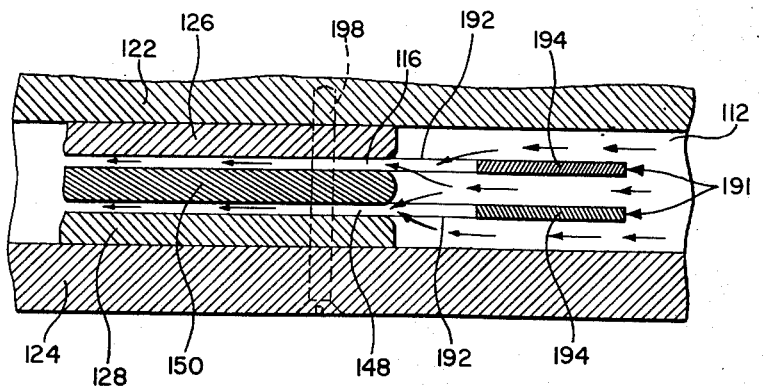
Figure 21:
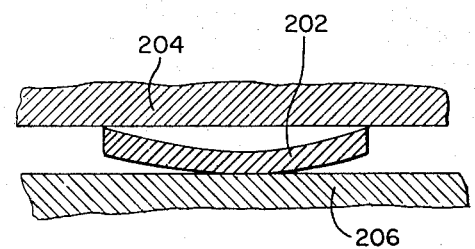
Figure 22:
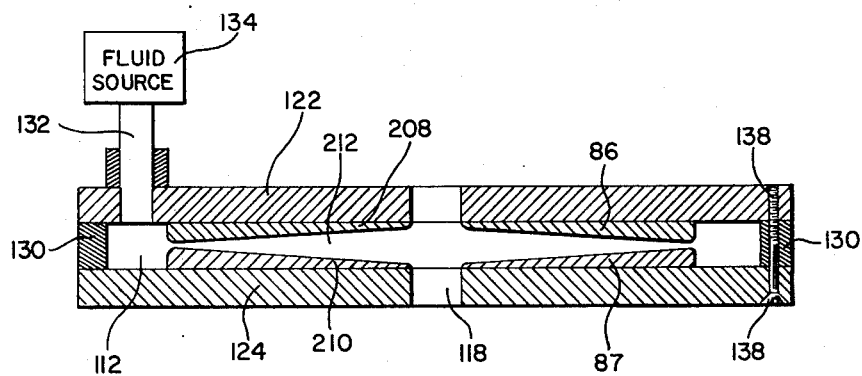
Figure 23:
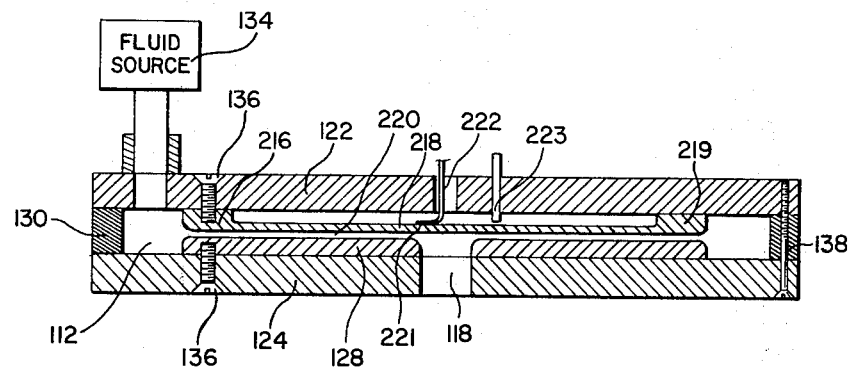
Figure 24:
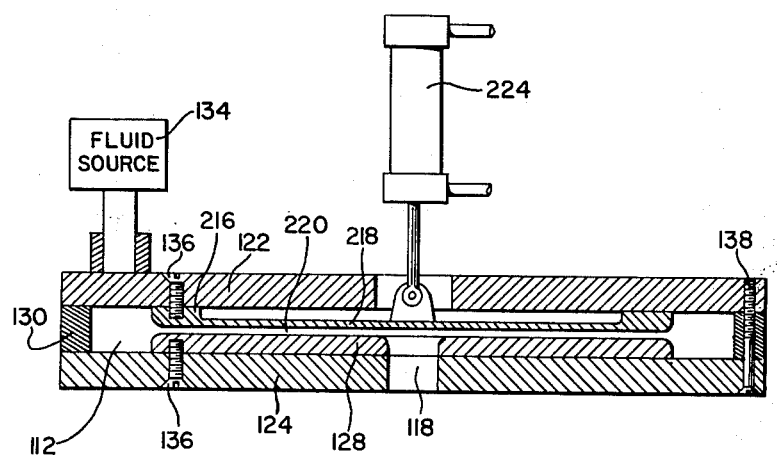

In the accompanying drawings which illustrate, by way of example, embodiments of the present invention, FIG. 1 is a graph showing the fluid shear stress plotted against the fluid shear rate for various fluids, FIG. 2 is a sectional side view along II—II, FIG. 3, of an apparatus for measuring the flow rate and/or viscosity of a fluid, FIG. 3 is a sectional plan view along III—III, FIG. 2, FIG. 4 is a graph of the output differential static pressure of the apparatus shown in FIGS. 2 and 3, plotted against the water mass flow rate therethrough, FIG. 5 is a graph of the output differential total pressure of the apparatus shown in FIGS. 2 and 3, plotted against the water mass flow rate therethrough, FIG. 6 is a sectional side view of an apparatus similar to that shown in FIGS. 2 and 3, but having two fluid passages, FIG. 7 is a sectional side view of a portion of the apparatus shown in FIG. 6, showing a total head probe, FIG. 8 is a sectional view along VIII—VIII, FIG. 7, of the total head probe, FIG. 9 is a sectional side view of a similar apparatus to that shown in FIGS. 2 and 3, but with static pressure taps, FIG. 10 is a sectional side view of a similar apparatus to that shown in FIGS. 2 and 3, but with a multiplicity of total pressure probes, FIG. 11 is a schematic view of a signal conditioning apparatus for use with the apparatus shown in FIG. 10, FIG. 12 is a plan view of a disc-shaped apparatus for measuring the flow rate and/or viscosity of a fluid, FIG. 13 is a sectional side view along XIII—XIII, FIG. 12, FIG. 14 is a plan view along XIV—XIV, FIG. 15, of a similar apparatus to that shown in FIGS. 12 and 13, but with more than one fluid passage, FIG. 15 is a sectional side view along XV—XV, FIG. 14, FIG. 16 is a sectional plan view along XVI—XVI, FIG. 17 of a similar apparatus to that shown in FIGS. 14 and 15, but with a plurality of radial spacers within the fluid passages, FIG. 17 is a sectional side view along XVII—XVII, FIG. 16, FIG. 18 is a sectional side view of a similar apparatus to that shown in FIGS. 16 and 17, but with a fluid inlet coaxial with a fluid outlet, FIG. 19 is a plan view of a shim for use with a disc-shaped apparatus such as shown in FIG. 13, for measuring the flow rate and/or viscosity of a fluid, FIG. 20 is a sectional side view along XX—XX, FIG. 19, which includes a portion of a disc-shaped apparatus for measuring the flow rate and/or viscosity of a fluid, and having a plurality of shims similar to the shim shown in FIG. 19, FIG. 21 is a sectional side view of a portion of a disc-shaped apparatus for measuring the flow rate and/or viscosity, illustrating a radial shim, FIG. 22 is a sectional side view of a similar apparatus to that shown in FIGS. 12 and 13, but with a fluid passage which tapers in thickness, FIG. 23 is a sectional side view of a disc-shaped apparatus for measuring the flow rate and/or viscosity of a fluid, and having a flexible wall for detecting radial static pressure distribution, and FIG. 24 is a sectional side view of a similar apparatus to that shown in FIG. 23, but with a diaphragm displacement device for adjusting the fluid passage geometry.

Referring now to FIG. 1, there are shown the characteristics of different fluids whose flow rates and/or viscous characteristics may be measured by the apparatus according to the present invention. In FIG. 1 the fluid shear stress is plotted vertically and the fluid shear rate horizontally. The curves 1 to 4 show the characteristics of four commonly referenced types of non-Newtonian fluids. Curve 1 represents a dilatant fluid, curve 2 represents a pseudoplastic fluid, curve 3 represents what is known as a Bingham plastic fluid, and curve 4 represents a fluid having a finite yield stress and a non-linear shear stress-shear rate curve. For comparison, an example of the corresponding shear stress vs shear rate characteristics for a Newtonian fluid is represented by curve 5.

Referring to FIGS. 2 and 3 an apparatus is shown for measuring the flow rate and/or the viscous characteristics of a fluid, comprising:

a. a casing, generally designated 6, having a fluid passage 8, a fluid inlet cavity 10 for connection to a source 40 of pressurized fluid and forming a substantially unobstructed flow path for fluid to the whole area of an inlet end 12 of the fluid passage 8, normal to the direction for flow of fluid in the fluid passage 8, and a fluid outlet cavity 14 forming a substantially unobstructed flow path for fluid from the whole area of an outlet end 16 of the fluid passage 8, normal to the direction for flow of fluid in the fluid passage 8.

b. fluid pressure detecting means, in the form of two fluid pressure detectors 18 and 20, in the casing 6 for detecting a fluid pressure differential between spaced positions in the fluid passage 8 in the direction (indicated by arrows in FIGS. 2 and 3) for flow of fluid therein, and c. fluid pressure indicating means, in the form of fluid pressure measuring instruments 22 and 24 connected to the detectors 18 and 20 from which the fluid pressure differential between the spaced positions in the fluid passage 8 can be deduced.

The apparatus has been found in practice to exhibit a useful output differential pressure dependency upon specific properties of the fluid flowing within the fluid passage 8 when the output differential pressure is measured by total pressure probes at the positions of the detectors 18 and 20 within the fluid passage 8, provided that:

1. the ratio of the mean breadth x (FIG. 3) to the mean width y (FIG. 2) of the area of the fluid passage 8, normal to the direction for flow therein, is at least ten to one for at least the portion of the fluid passage 8 which extends between the spaced positions of the fluid pressure detectors 18 and 20 therein, whereby flow through the fluid passage 8 is maintained essentially two-dimensional, and 2. the area of the fluid passage 8 normal to the direction for flow of fluid in the fluid passage 8, and for at least the portion of the fluid passage 8 which extends between the said spaced positions continuously reduces in size such that laminar flow is maintained over a Reynolds number range in excess of that attainable within a parallel flow fluid passage as evidenced by the output total differential pressure dependency upon the flow rate of substantially pure water, for example distilled water, at 70°F conforming to the relationship in consistent units:

$$\Delta P = K_3 G$$

over a range of flow rates such that the maximum Reynolds number in the fluid passage 8 between the detectors 18 and 20 is varied between 0 and 8000 where the Reynolds number and G are as previously defined and where:

$\Delta P$ = output differential total pressure as defined by the difference in total pressure between the locations of the two detectors 18 and 20.

$K_3$ = coefficient dependent upon the fluid density, the fluid viscosity and the geometry of the fluid passage 8.

Such a relationship between output differential total pressure ($\Delta P$) and mass flow rate (G) is illustrated in FIG. 5 where the relationship parameters are identified.

It has been found convenient in practice to numerically evaluate the geometry of the fluid passage 8 limiting criteria as per provisions (1) and (2) above when the output differential pressure is measured by total pressure probes within the fluid passage 8 at the two locations of the two detectors 18 and 20 by means of the following procedure:

The mass flow rate of water at 70°F corresponding to a maximum Reynolds number of 3500 and 8000, within the fluid passage 8 between detectors 18 and 20 as defined by the total pressure detection locations, is determined using any well-known measurement means such as a rotameter for the particular flow passage geometry where the absolute viscosity and the density of substantially pure water, for example distilled water, at 70°F may be taken, in English units, to be $0.210 \times 10^{-4}$ lbs. sec/ft.$^2$ and 62.4 lbs./ft.$^3$ respectively.

The output differential total pressures for water mass flow rates corresponding to maximum flow passage Reynolds numbers of 3500 and 8000, are determined using any well-known pressure measurement means.

The previously defined coefficient $K_3$ is numerically evaluated from the output differential total pressure measurement and corresponding mass flow rate in accordance with the relationship in consistent units:

$$K_3 = \Delta P_1/G_1$$

where the subscript 1 refers to the appropriate measured mass flow rate or total pressure differential at a fluid passage 8 maximum Reynolds number of 8000, as defined in FIG. 5.

The output differential total pressure measured at a water mass flow rate corresponding to a fluid passage 8 maximum Reynolds number of 3500 is compared with the pressure differential calculated from the relationship in consistent units:

$$\Delta P_2 = K_3 G_2$$

where $G_2$ is the measured water mass flow rate at a fluid passage 8 maximum Reynolds number of 3500 and where $K_3$ is the previously defined coefficient numerically evaluated as per the procedure given above. The laminar flow criterion as per the geometry limiting provision (2) previously defined of the fluid passage 8 is satisfied when the calculated and measured total pressure differentials do not deviate one from the other by more than the experimental error of such pressure and flow measuring devices as may be used.

Should the deviation between the calculated and measured total pressure differentials exceed the experimental error of the said measuring devices whereby the laminar flow criterion is violated, then the said criterion could be satisfied by a further reduction in the fluid passage area, normal to the direction for flow, in the fluid flow direction. This can be achieved by means of a further reduction in the direction of flow of the fluid passage width or of the fluid passage mean breadth or of both the fluid passage mean width and mean breadth as previously defined.

The casing 6 comprises a top plate 26, a bottom plate 28, top and bottom spacers 30 and 32, and a thin, profiled shim 34 which defines both the mean width and reduction in crosssectional area of the fluid passage 8. The spacers 30 and 32 and profiled shim 34 are rigidly located relative to and are clamped between the plates 26 and 28 by screws 36, and if desired by suitable dowel pins (not shown).

The fluid inlet cavity 10 is connected by a pipe 38 to the source 40 of pressurized fluid.

The fluid pressure detectors 18 and 20 are total or impact pressure detectors and are preferably located in the fluid passage 8 adjacent to the fluid inlet cavity 10 and fluid outlet cavity 14 respectively, and are also preferably located at positions along the axis of symmetry of the fluid passage 8 in the direction for flow of fluid therealong.

The fluid pressure detectors 18 and 20 may each be any well known total pressure detector such as a total head tube, connected to a manometer, pressure gauge, or electrical, pneumatic or mechanical pressure transducer or similar device.

In operation, fluid from the pressurized fluid source 40 flows into the fluid inlet cavity, along the fluid passage 8 and out of the apparatus via the outlet cavity 14. The fluid inlet total pressure to the fluid passage 8 is detected by the fluid pressure detector 18 and indicated on instrument 22, and the fluid outlet total pressure from the fluid passage 8 is detected by the fluid pressure detector 20 and indicated on instrument 24. By subtracting the fluid pressure indicated by instrument 24 from that indicated by instrument 22 the output differential total fluid pressure in the fluid passage 8 is obtained.

The apparatus shown in FIGS. 2 and 3 has also been found in practice to exhibit a useful output differential pressure dependency upon specific properties of the fluid flowing within the fluid passage 8 when the said output differential pressure is measured by detectors in the form of fluid passage wall static pressure taps such as in the apparatus illustrated in FIG. 9 where static pressure taps are shown located at two spaced positions 76 and 78 which define a passage flow length, provided that:

3. the ratio of the mean breadth to the mean width of the fluid passage 8, normal to the flow direction is at least ten to one for at least the portion of the fluid passage 8 between the detectors 76 and 78 whereby essentially two-dimensional flow is maintained through the passage.

4. the reduction in the flow direction of the crosssectional area of the fluid passage 8, normal to the flow direction over at least the portion of the fluid passage 8 between the detectors 76 and 78 is such that laminar flow is maintained over a Reynolds number range in excess of that attainable within a parallel flow passage as evidenced by the output differential static pressure dependency upon the flow rate of substantially pure water at 70°F conforming to the relationship in consistent units:

$$\Delta p = K_1 (G)^2 + K_2 (G)$$

over a range of flow rates such that the maximum Reynolds number within the fluid passage 8 is varied between 0 and 8000, where the Reynolds number is as previously defined and where the coefficient ratio $(K_1/K_2)$ is greater than 0.01 and where $\Delta p$ = output differential static pressure between the specified detection locations, and $K_2$ = coefficient dependent upon the fluid density, the fluid viscosity, and the passage geometry $K_1$ = coefficient dependent upon the fluid density and the passage geometry Such a relationship between output differential static pressure ($\Delta p$) and mass flow rate (G) is illustrated in FIG. 4 where the relationship parameters are identified, and it will be readily apparent to those skilled in the art that for a known fluid flowing along the fluid passage 8, the flow rate and/or viscosity of that fluid can be deduced from the pressure differential between the detectors 76 and 78.

It has been found convenient in practice to numerically evaluate the fluid passage geometry limiting criteria given above when the output differential pressure is measured by passage flow wall static pressure taps at the two passage length defining pressure detection locations by means of the following procedure:

a. using distilled water as the substantially pure water, the mass flow rate of the distilled water at 70°F corresponding to a maximum Reynolds number of 3500, 7000 and 8000, within the fluid passage flow length, between the detector locations, is determined using any well-known measurement means such as a rotameter for the particular fluid passage geometry where the absolute viscosity and the density of pure water at 70°F may be taken, in English units, to be $0.210 \times 10^{-4}$ lbs.sec/ft.$^2$ and 62.4 lbs./ft.$^3$ respectively.

b. the output differential static pressures for water mass flow rates corresponding to maximum flow passage Reynolds numbers of 3500, 7000 and 8000 are determined using as pressure detectors any well-known pressure measurement means such as manometers.

c. the coefficients $K_1$ and $K_2$ are numerically evaluated, from the output differential static pressure measurements and corresponding mass flow rates in accordance with the relationships in consistent units:

$$K_2 = \frac{\Delta P_1 - \Delta P_2 \left(\frac{G_1^2}{G_2}\right)}{G_1 - \frac{(G_1)^2}{G_2}}$$

and $$K_1 = \frac{\Delta P_1 - K_2(G_1)}{(G_1)^2} = \frac{\Delta P_2 - K_2(G_2)}{(G_2)^2}$$

where, as stated previously, the subscripts 2 and 1 refer to the appropriate measured mass flow rate or static pressure differential at fluid passage 8 maximum Reynolds numbers of 3500 and 8000, respectively, as identified in FIG. 4.

d. the output differential static pressure measured by the detectors at a water mass flow rate corresponding to a maximum Reynolds number of 7000 within fluid passage 8 is compared with the pressure differential calculated from the relationship in consistent units:

$$\Delta p = K_1(G_3)^2 + K_2(G_3) \qquad 3.$$

where $G_3$ is the measured water mass flow rate at a fluid passage 8 maximum Reynolds number of 7000 and where $K_1$ and $K_2$ are the previously defined coefficients numerically evaluated as per the procedure given above. The laminar flow criterion as per the fluid passage 8 geometry limiting provisions (3) and (4), previously defined, is satisfied when the calculated and measured static pressure differentials do not deviate one from the other by more than the experimental error of such static pressure and flow measuring devices as may be used and when the coefficient ratio $K_1/K_2$ is greater than 0.01 where $K_1$ and $K_2$ are the previously defined coefficients numerically evaluated as per the procedure given above.

Should the deviation between the calculated and measured static pressure differentials exceed the experimental error of the said measuring devices or should the coefficient ratio $K_1/K_2$ be less than the specified value, then the fluid passage geometry constraining provisions could be satisfied by a further reduction in the fluid flow direction of the fluid passage area normal to the direction for flow by means of a further reduction in the direction of flow of the fluid passage mean breadth or of the fluid passage mean width or of both the fluid passage mean breadth and mean width as previously defined.

This apparatus according to the FIGS. 2 and 3 is referred to hereafter as a "convergent fluid passage sensor" in that it uses the favourable pressure gradient in the flow direction as generated by the geometric convergency to maintain laminar flow within the fluid passage 8 over a substantial Reynolds number range. This differentiates the convergent, fluid passage sensor from flow sensors based on the viscous resistance to flow through purely parallel passages as described in Ricardo et al, Fluid Flow Meter, U.S. Pat. No. 2,212,186, dated Aug. 20, 1940, or from flow sensors based on the resistance to flow through the gaps between a multitude of spheres or other particles as described in Franklin Institute, Research Laboratories of Philadelphia, Pa., Report I-A2049-24, or from sensors based on the viscous resistance to flow through passages diverging in the direction of flow as described in Sarem, Flow Rate Measuring Device, U.S. Pat. No. 3,040,570, dated June 26, 1962, and in Posingies, Fluid Vortex Angular Motion Sensor, U.S. Pat. No. 3,590,643, dated July 6, 1971, FIGS. 1 and 2.

The operational principle of the convergent fluid passage sensor can be most easily understood by considering a thin rectangular, fluid passage of constant width where the passage breadth decreases linearily with respect to the passage flow length at a rate which satisfies the defined geometry limiting provisions 1) to 4) inclusive.

A pressurized fluid souce is coupled to the larger cross sectional area end of the fluid passage so as to induce flow through the fluid passage in the direction of reducing, fluid passage cross-sectional area. Fluid flowing through such a convergent fluid passage will experience an energy loss as evidenced by a gradient in total pressure in the direction of flow, where this energy loss is the result of viscous shearing between the fluid and fluid passage walls.

In the particular case of a Newtonian fluid, the distribution of viscous energy dissipation results in a total pressure drop along the fluid passage flow length which is dependent on the geometry of the fluid passage 8 and the density, viscosity, and flow rate of the fluid in accordance with the relationship in consistent dimensions:

$$\Delta P = K \mu G / \rho$$

where K is a coefficient dependent only upon the geometry of the fluid passage 8, and where $\mu$, G and $\Delta p$ are as defined previously.

In the absence of a significant static pressure gradient in the direction of flow, this relationship is limited to a Reynolds number of less than approximately 7000 for two-dimensional flow where the Reynolds number is as defined previously.

In the presence of a significant decreasing static pressure (i.e., total minus dynamic pressure) gradient in the direction of flow associated with the accelerating flow field within the convergent fluid passage, the maintenance of laminar flow is not limited to Reynolds numbers of less than approximately 7000 as in the case of two-dimensional parallel flow, but may be extended to appreciably higher Reynolds numbers, the magnitude of which will be dependent on the static pressure gradient in the direction of flow in addition to characteristics of disturbances within the flow (i.e., disturbance wave length, intensity, etc.).

In the present apparatus, a substantial fluid passage cross-sectional area reduction gradient with respect to the fluid passage length in the flow direction is advantageous in that such an area reduction will result in the range of linear dependency of the output total pressure differential upon mass flow rate being considerably larger and the output total pressure differential sensitivity to fluid viscosity variation being considerably greater than that associated with parallel flow or particle bed dependent flow devices with equivalent fluid flow passage mean cross-sectional area. Conversely, such an area reduction is advantageous from the practical consideration of fluid passage tolerance to fluid solid particle contamination in that a larger fluid passage mean width may be used than that associated with parallel flow or particle bed dependent flow devices with equivalent output pressure differential sensitivities.

The energy dissipation flow length of the fluid passage may be directly measured in terms of a total pressure differential where total head pitot tubes or probes of suitable configuration may be appropriately located within the fluid passage defined by the apparatus.

It can be seen from the above total pressure relation that the detected total pressure differential will be directly proportional to the mass flow rate for fixed fluid viscosity and standard density or to the volumetric flow rate for fixed fluid viscosity. Herein, the term "standard density" is understood to mean fluid specific weight referenced to a fixed standard of fluid temperature and pressure. It can be additionally seen that the detected total pressure differential will be directly proportional to the absolute viscosity of the fluid for a given volumetric flow rate provided the fluid is effectively Newtonian and provided a total head pitot tube or probe is at a position in the fluid passage such that the detected pressure differential is measurably sensitive to variations of fluid viscosity.

In practice it may be convenient fluid measure energy dissipation along the flow length of the flow passage in terms of static rather than total pressure wherein conventional wall static pressure taps or flush mounted pressure transducers are located on the fluid passage wall.

The relation between the fluid viscous energy loss, in the fluid passage as evidenced by the total pressure differential, the detected static pressure differential and the change in dynamic pressure, is defined by the well-known Bernoulli relation in consistent units:

$$\Delta P = \Delta p + \Delta(\tfrac{1}{2}\rho U^2) = \Delta p + \Delta \left[ \frac{G^2}{2\rho A^2} \right]$$

where $\Delta P$, $\Delta p$, $\rho$, G and U are as previously defined and where:

$\Delta(\tfrac{1}{2}\rho U^2)$ = change in dynamic pressure in the fluid passage between the locations of the detectors.

A = fluid passage cross-sectional area normal to the flow direction.

Accordingly, the sensed static pressure drop across the fluid passage will reflect velocity changes through the fluid passage as well as viscosity induced energy dissipation in accordance with the above relationship.

The degree of dominance of the viscosity induced pressure differential as defined by $K\mu G/\rho$ relative to the Bernoulli pressure differential as defined by $\Delta(\tfrac{1}{2}\rho U^2)$ will be dependent on the particular geometric configuration of the fluid passage.

It can be seen that for a Newtonian fluid that where the viscosity-induced pressure differential tends to dominate, the static pressure differential will approach direct proportionality to the mass flow rate for a fixed fluid viscosity and standard density or to the volumetric flow rate for fixed fluid viscosity.

It can be further seen that for a Newtonian fluid that where the Bernoulli effect tends to dominate, the static pressure differential will approach direct proportionality to the square of the mass flow rate for fixed fluid viscosity and standard density, or to the square of the volumetric flow rate for fixed fluid viscosity.

It can be additionally seen for a Newtonian fluid that where the viscosity-induced pressure differential tends to dominate, the static pressure differential will approach direct proportionality to the absolute viscosity of the fluid, for a given volumetric flow rate and will approach direct proportionality to the mass flow rate for fixed fluid viscosity and standard density.

It will be evident from the above observations that by suitable reduction of the cross-sectional area of the fluid passage, variations in static pressure in the direction of flow, resulting from variations in the local fluid viscous shear distribution, will provide a wide range of performance characteristics.

In the particular case of a non-Newtonian fluid, the distribution of viscous energy dissipation along the fluid passage will be a unique function of the absolute shear-stress shear-strain relationship of the fluid for a given mass flow rate, this unique function having significant range when the fluid passage geometry is such that an appreciable variation of fluid viscous shear rate is generated through the fluid passage. One commonly used model relating to the shear stress and the shear rate of a time independent non-Newtonian fluid without a yield stress is the "power law model" as given by the relationship, in consistent dimensions:

$$\tau_{hx} = \frac{\mu_a}{g} \left[ \frac{dU}{dh} \right]^n$$

where $g$, $U$ and $h$ are as previously defined and where:

$\tau hx$ = fluid shear stress acting along the fluid passage flow length upon the passage bounding surface perpendicular to the passage mean width direction $\mu_a$ = apparent viscosity $dU/dh$ = fluid viscous shear rate (i.e., slope of the radial velocity distribution across the fluid passage mean width $n$ = dimensionless fluid index It can be seen that this shear stress equation that by the appropriate selection of the fluid passage cross-sectional area reduction, the distribution of the fluid mean shear rate ' $dU/dh$ ' along the fluid passage flow length may be altered significantly. An associated shear stress dependent viscous energy dissipation will generate a pressure distribution along the fluid passage flow length which will, in turn, exhibit a unique dependency upon the fluid non-Newtonian properties as characterized by the apparent viscosity '$\mu_a$' and the fluid index '$n$'. It will be appreciated that non-Newtonian fluids as described by more complex models relating the fluid shear stress and the shear rate such as those commonly referred to as the Ellis, the DeHaven, the Prandtl-Eyring models, etc., will also exhibit useful ranges of pressure distributions along the fluid passage flow length which are uniquely dependent upon the appropriate model-defining parameters when the fluid passage cross-sectional area reduction is selected to attain a significant fluid shear rate variation in the flow direction.

In accordance with the present invention, a particularly useful function is the continuous monitoring of the static or total pressure distribution along the fluid passage flow length as generated by the flow of non-Newtonian fluids, such as lubricants, food products, wood pulp slurries, etc., where the shear stress to shear rate relationship is a critical performance parameter. Any specified tolerance band applied to the shear stress/shear rate relationship of such non-Newtonian fluids may be analytically converted to an equivalent apparatus lengthwise pressure distribution tolerance band wherein the specified tolerance may be monitored directly in terms of the apparatus output pressure distribution. The apparatus may be either intermittently supplied with a fluid for individual sample testing or may be continuously supplied for on-line process monitoring applications.

It is therefore possible with the apparatus according to the present invention to measure the flow rate of fluids, or the viscosity of Newtonian fluids, or the viscous characteristics of non-Newtonian fluids, either as singular measurements or in combination with the measurement of other properties, to provide useful information regarding the characteristics of such fluids.

The advantages of the present invention as compared to existing devices for performing similar measurements of flow, or viscosity, or non-Newtonian characteristics, are numerous. Some of these advantages, which will become increasingly apparent with subsequent descriptions of embodiments of the present invention, are listed below for devices having essentially rectangular fluid passage cross-sections normal to the flow direction.

1. Economical to manufacture in either small or large quantities relative to the performance potential in terms of output sensitivity and/or linearity in that a wide range of planar flow, fluid passage defining elements may be common to a particular sensor housing or structural element and may be fabricated by a number of well-established techniques with a minimum of non-recurring costs.

2. A very wide range of performance with both liquids and gases, in terms of output sensitivity, flow capacity, or viscosity range, can be attained within a single housing or structural element by addition, removal or replacement of low cost planar flow, fluid passage defining elements. This furthers standardization and minimizes sensor hardware stock requirements.

3. Ease of disassembly and/or replacement of fluid passage defining elements facilitates inspection, cleaning and maintenance.

4. Output dynamic range, as defined by the maximum usable output signal divided by the minimum signal detectable within the output noise, can be very large when full advantage is taken of the inherent noise suppression characteristics of accelerating laminar flow.

5. Continuous operation with the same fluid or intermittent operation with the same or different fluids is feasible, the apparatus being essentially self-purging.

6. Inherent large surface area compared to the cross-sectional area normal to the flow direction within the fluid passage facilitates compensation of flow induced heat loss and regulation of the fluid temperature.

7. When used as a flowmeter, the output is directly proportional to the volumetric flow rate when the differential total pressure over the fluid passage flow length is the output.

8. When used as a viscometer with Newtonian fluids, the output is directly proportional to the absolute viscosity for a given volumetric flow rate when the differential total pressure over the fluid passage flow length is the output.

9. The apparatus generates continuous pressure distribution readings which provide an indication of the shear stress versus shear rate characteristics for non-Newtonian fluids over an extended shear rate range. Additionally, non-Newtonian fluids which exhibit time dependent viscosity characteristics may be continously monitored.

It will be appreciated that the wide range of performance claimed for this invention as per advantages 2, 4, 7, 8 and 9 listed above, may be extended by suitable contouring of the laminar flow, fluid passage defining elements.

Additional advantages to those listed above for apparatus according to the present invention, having adjustable of flexible flow defining elements are listed below:
1. In situ adjustment of range in terms of output sensitivity may, within limits, be made through external adjustment. 2. The use of partially or wholly flexible plates to define the fluid passage allows for an indication of the static pressure distribution within the fluid passage by direct measurement of the strain or deflection of the flexible plates by means of such well-known techniques as resistance strain qauging or air gauging.

Returning now to the apparatus shown in FIGS. 2 and 3, it will be appreciated that the performance of such apparatus, or any other according to the present invention, is not in general dependent upon the orientation of the apparatus in that compensation for orientation of the apparatus will not be required unless hydrostatic head effects vary significantly either along or across the flow length of the fluid passage 8 for laminar flow therethrough. For example, such hydrostatic head variations might be encountered in the particular case of a large scale apparatus operating with a high density fluid and orientated with the fluid passage flow axis of symmetry vertical. An apparatus according to the present invention and having a plurality of similar fluid passages in parallel, such as will be described later with reference to other figures, may also be affected by hydrostatic head variations in the same manner.

With fixed fluid properties of absolute viscosity and density, the apparatus shown in FIGS. 2 and 3 will function as a fluid mass flow meter in that the pressure differential measured by the detectors 18 and 20 in the form of total pressure probes will be directly proportional to the fluid mass flow rate through the apparatus, provided the flow within the fluid passage 8 is laminar.

With a fixed fluid property of absolute viscosity, the apparatus shown in FIGS. 2 and 3 will function as a fluid volumetric flow meter in that the pressure differential measured by the detectors 18 and 20 in the form of total pressure probes will be directly proportional to the fluid volumetric flow rate through the apparatus, provided the flow within the fluid passage 8 is laminar.

With a fixed density fluid and with the pressurized fluid source 40 regulated so as to maintain a constant mass flow rate through the fluid passage 8, the apparatus will function as a viscometer in that the pressure differential as measured by the detectors 18 and 20 in the form of total pressure probes will be directly proportional to the fluid viscosity, provided the flow within the fluid passage 8 is laminar. For such a constant mass flow rate source of fixed density fluid, the pressurized fluid source 40 might be comprised of a positive fixed displacement pump such as a hydraulic axial-piston pump operating at a constant rotational speed.

With a variable density fluid, where the density exhibits dependency upon both the fluid temperature and pressure, and with the pressurized fluid source 40 regulated so as to maintain a constant total pressure and temperature at the inlet end 12 of the fluid passage 8, and with the outlet cavity 14 exhausting to a fixed reference pressure, such as the atmosphere, the apparatus will function as a viscometer provided that the detector 20 is a total pressure probe and is located between the fluid passage inlet 12 and outlet 16 preferably on the axis of symmetry of the flow passage and preferably at a passage lengthwise position, in the direction of flow, such that the sensitivity of the detected total pressure to fluid viscosity variation is measurable, and preferably is a maximum. The total pressure detected by such a detector 20 will be a unique but typically nonlinear function of the fluid viscosity, provided the flow within the fluid passage 8 is laminar. The degree of non-linearity of the total pressure dependency upon fluid viscosity is a complex function of the mean width, cross-sectional area reduction gradient, fluid inlet pressure and fluid flow rate of the fluid passage 8 as will be evident either from experimental testing of the apparatus or from such analytical prediction of the apparatus performance as may be derived.

In FIG. 6, similar parts to those shown in FIGS. 2 and 3 are designated by the same reference numerals, and the previous description is relied upon to describe them.

FIG. 6 is a cross-sectional side view of an apparatus similar to that shown in FIGS. 2 and 3 except that there are two identical fluid passages 46 and 48 which reduce in cross-sectional area, in the direction of fluid flow therealong. The inlet cavity 50 feeds fluid into the two fluid flow passages 46 and 48, which exhasut into a common fluid outlet cavity 52. The cavities 50 and 52 and fluid passages 46 and 48 are defined by the spacers 30 and 32 and a spacer 54 and two profiled shims 56 and 58 alternatively stacked between top plate 26 and bottom plate 28. The spacers 30, 32 and 54 are identical. Two total pressure probes 60 and 62 are provided as the two fluid pressure detectors and are located within the fluid passage 46 near the fluid passage inlet end 64 and outlet end 66.

In operation the apparatus shown in FIG. 6 functions in the same manner as the apparatus shown in FIGS. 2 and 3 except that fluid flows along both of the fluid passages 46 and 48, and the pressure differential is only measured in the fluid passage 46.

The embodiment shown in FIG. 6 operates in the same manner as the embodiment described with reference to FIGS. 2 and 3, but can handle larger flow rates provided that the portion of the fluid flowing through the fluid passage 48 has the same flow characteristics therealong as the portion of the fluid flowing along the fluid passage 46.

It will be appreciated that with an apparatus as shown in FIG. 6 or with an apparatus similar to that shown in FIG. 6 but having more than two parallel coupled, identical fluid passages, total pressure probes could be located within any one or any number of the flow passages in that the total pressure distribution, in the direction of flow, within all of the fluid passages will be the same.

In FIGS. 7 and 8 similar parts to those shown in FIG. 6 are designated by the same reference numerals and the previous description is relied upon to describe them.

A specific total head pressure probe configuration is shown in FIGS. 7 and 8, where two of these probes are particularly useful in detecting the total pressure differential between any given locations within one or more identical flow passages with configurations of the apparatus as shown in FIGS. 2 and 3, or in FIG. 6, or in configurations similar to that shown in FIG. 6, but having more than two identical fluid passages. With reference to FIG. 7, a total head probe tube 68, is fixed within the apparatus by some suitable means such as a screw threaded plug 70 threaded in the aperture 72 in top plate 26, and sealed therein by an 'O'-ring 71, and passing through spacers 30, 32 and 54 so as to traverse the two fluid passages 46 and 48. A narrow longitudinal slot 74 is cut along a portion of the length of tube 68, and a section through the slotted tube is shown in FIG. 8. The probe tube 68 is located such that the slot 74 is oriented towards and is essentially perpendicular to the fluid flow direction within the fluid passages 46 and 48, as shown by the arrows in FIG. 7.

It will be appreciated that in both the single and multiple fluid passage embodiments of the apparatus as shown in FIGS. 2 and 3 or 6, the shims designated 34 (FIGS. 2 and 3) and 56 and 58 (FIG. 6) could have fluid passage profiles differing in plan view from the straight tapering profiles shown provided that the fluid passage cross-sectional area normal to the fluid flow direction continuously reduces in the direction of flow over at least the portion of the fluid passage between the total head pressure probes.

A further embodiment of the invention comprises essentially the same parts as shown in FIGS. 2 and 3, or in FIG. 6, except that the detectors 18 and 20 or 60 and 62 are wall static pressure taps. In FIG. 9 there is shown a sectional side view of such an embodiment and similar parts to those shown in FIGS. 2 and 3 are designated by the same reference numerals and the previous description is relied upon to describe them. In this embodiment the detectors are in the form of static pressure taps 76 and 78 located adjacent to the fluid inlet cavity 10 and fluid outlet cavity 14 respectively.

It will be appreciated that it is within the scope of the present invention for one or both static pressure taps 76 and 78 instead of being within the fluid passage 8, to be located at the wall of the cavities 10 or 14 connecting with the fluid passage 8 as in the case of static pressure tap 80 being located within the fluid inlet cavity 10 and static pressure tap 82 located in the fluid outlet cavity 14 provided that any flow static pressure variation in the cavities 10 and 14 between the static pressure taps 80 and 82 and the fluid passage entrance or exit respectively is not significant relative to the static pressure differential along the fluid passage 8 for any particular operational mode of the apparatus. The existence of such flow static pressure variation for any given operational mode of the apparatus may be determined experimentally or on the basis of information provided in standard texts.

It will be appreciated that in the configuration of the apparatus illustrated in FIG. 9, as well as in additional embodiments of the invention described herein, the pressure detected by a static pressure tap within either the inlet or the outlet cavity will be substantially identical to the pressure detected by a total pressure probe provided that the fluid velocity in the immediate vicinity of the cavity pressure detection location is low relative to the minimum velocity within the fluid flow passage. Accordingly, a static pressure tap within the inlet or outlet cavity of the apparatus may be considered the equivalent of a total pressure probe within the limits of the specified cavity velocity constraints. Thus one or more static pressure taps may be used with one or more total pressure probes.

For the embodiment shown in FIG. 9, pressure taps for the measurement of wall static pressure of the fluid passage 8 may be interpreted to mean any well-known method of static pressure measurement. Such methods would include flush-mounted pressure transducers or holes in the spacer 30 leading from the surface thereof bounding the fluid passage 8 and connected to a suitable pressure measuring instrument 22 or 24 or in the bottom plate 28 leading from the surface thereof bounding the fluid inlet cavity 10 and outlet cavity 14 and connected to a suitable pressure measurement instrument 84 or 86, where such an instrument might be a manometer, pressure gauge, electrical, pneumatic or mechanical pressure transducer or similar device.

With a fixed absolute viscosity fluid, the apparatus shown in FIG. 9 will function as a fluid flow meter in that the pressure differential as measured either between the static pressure taps 76 and 78 within the fluid passage 8, or between pressure taps 80 and 82 upstream and downstream of the fluid passage 8, or between pressure taps 76 and 82, or between pressure taps 80 and 78, will be a unique but typically non-linear function of either the mass flow rate or of the volumetric flow rate through the apparatus. Even through pressure taps 80 and 82 are positioned outside the fluid passage 8 they are measuring the static pressure at the end of the fluid passage 8 to which they are adjacent. The degree of non-linearity is a complex function of the mean width and crosssectional area reduction gradient of the fluid passage 8 and the fluid flow rate range therealong as will be evident either from experimental testing or theoretical analysis.

With a fixed density fluid and with the pressurized fluid source 40 regulated so as to maintain a fixed mass flow rate through the fluid passage 8, the apparatus shown in FIG. 9 will function as a viscometer in that the static pressure differential as measured for the fluid flow meter function defined above will be directly proportional to the fluid viscosity provided the flow in the fluid passage 8 is laminar.

With a variable density fluid where the density exhibits dependency upon both the fluid temperature and pressure, and with the fluid source regulated so as to maintain a constant total pressure and temperature at the inlet or flow passage 8, and with the fluid exhausting from the fluid chamber to a constant reference pressure such as to the atmosphere, the apparatus will function as a viscometer provided that the static pressure probe 78 shown near the outlet of the fluid passage 8 in FIG. 9 is relocated upstream to a position between the inlet 10 and the outlet 14 of the fluid passage 8 at a passage position in the direction of flow position such that the sensitivity of the detected static pressure to fluid viscosity variation is measurable and preferably is a maximum. The static pressure detected by such a relocated pressure probe 78 will be a unique but typically non-linear function of the fluid viscosity provided the flow within the fluid passage 8 is laminar. The degree of non-linearity of the static pressure dependency upon fluid viscosity is a complex function of the width and cross-sectional area reduction gradient of the fluid chamber 8, the fluid inlet pressure thereto and fluid flow rate therealong as will be evident either from experimental testing or theoretical analysis.

Yet a further configuration of this invention which has particular application in the measurement of the shear stress/shear rate viscous characteristics of non-Newtonian fluids is shown in FIG. 10, where similar parts to those shown in FIGS. 2 and 3 are designated by the same reference numerals and the previous description is relied upon to describe them. A multiplicity of total pressure probes 90 to 95 are distributed in the fluid passage 8 in the direction of flow of fluid and between the inlet cavity 10 and outlet cavity 14. Each total pressure probe 90 to 95 is connected to a pressure measuring instrument 98 to 103 respectively, such as a manometer, pressure gauge or similar device so as to provide a means of measuring the distribution of total pressure across the fluid passage 8.

Such a total pressure distribution will be a unique function of the absolute stress-strain relationship of the non-Newtonian fluid flowing within the fluid passage 8 when the pressurized fluid source 40 is regulated such that the mass flow rate through the apparatus is constant. The constant mass flow rate source may be a positive fixed displacement pump such as a hydraulic axial-piston pump operating at constant rotational speed in that the density of non-Newtonian fluids is constant.

It will be appreciated that this measured total pressure distribution will be useful in indicating the degree of conformity of the shear stress-shear rate viscous characteristics of a specific non-Newtonian fluid with that of a reference non-Newtonian fluid when the cross-sectional area reduction of the fluid passage 8 is such that a significant distributed variation of fluid viscous shear rate is generated along the flow length of the fluid passage 8 in that the total pressure distribution in the fluid passage 8 may be analytically predicted from the known non-Newtonian characteristics of the reference fluid or experimentally determined using the reference fluid in the test apparatus.

In FIG. 11, similar parts to those shown in FIG. 10 are designated by the same reference numerals and the previous description is relied upon to describe them.

Improvement in the interpretation of the total pressure distribution in the fluid passage 8, in relation to the absolute stress-strain characteristics of the fluid flowing along the fluid passage 8 may be attained as shown in FIG. 11, by the use of a signal conditioning apparatus, such as a digital computer 106, and an associated display or readout apparatus, such as an X—Y plotter 108. The computer 106 is coupled via the pressure measuring instruments 98 to 103, which in this embodiment are fluid pressure transducers, to the total pressure probes (not shown) within the fluid passage (not shown).

It will be appreciated that, in a different embodiment of the present invention, the apparatus is generally as described with reference to FIGS. 10 and 11, except that the total pressure probes 90 to 95 are replaced by static pressure taps on the wall of the fluid passage 8 such as the static pressure taps described with reference to FIG. 9. In this embodiment the use of the apparatus is also for indicating non-Newtonian fluid characteristics.

In FIGS. 12 and 13 there is shown a cylindrical casing 110 having an outer, annular shaped fluid inlet cavity 112 forming a substantially unobstructed flow path for fluid to flow radially inwardly to the whole outer periphery of the inlet end 114 of an intermediate annular shaped fluid passage 116 and an inner, annular shaped fluid outlet cavity 118 forming a substantially unobstructed flow path for fluid flowing radially inward from the whole inner periphery of the outlet end 120 of the fluid passage 116. The casing 110 comprises a top disc plate 122, a bottom disc plate 124, top and bottom ring spacers 126 and 128, respectively, and an outer, circumferential ring 130. The inlet cavity 112 is connected by one or more inlet pipes, one being shown and designated 132, to a pressurized fluid source 134. The plates 122 and 124, spacers 126 and 128, and outer ring 130, are rigidly secured relative to each other by means of screws 136 and 138, and if desired by suitable dowel pins (not shown), so as to define the inlet cavity 112, fluid passage 116 and outlet cavity 118. Two total pressure probes 140 and 142, similar to the probes 18 and 20 shown in FIG. 2, are located near the inlet end 114 and outlet end 120, respectively, of the fluid passage 116. Fluid pressure transducers 144 and 146 are connected to the probes 140 and 142 respectively.

In operation pressurized fluid from the source 134 enters the inlet cavity 112 through the inlet pipe 132, and flows radially inward through the fluid passage 116 in a laminar flow mode leaving the fluid passage 116 through the fluid outlet cavity 118, as shown by the arrows in FIG. 13. The total pressure probes 140 and 142 are used to measure the flow rate and/or the viscous characteristics of the fluid flowing in the fluid passage 116 and in this instance the mean width is the mean distance between spacers 126 and 128, while the mean breadth is the circumference the fluid passage 116 at any given radius from the axis of symmetry.

It should be noted that the apparatus described with reference to FIGS. 12 and 13, does not incorporate any means of detecting or measuring the angular velocity or vorticity of the flow either within the fluid passage 116 or the outlet cavity 118 nor does the apparatus incorporate any structural means between the inlet cavity 112 and the fluid passage 116 for coupling the direction of fluid flow with rotational motion of the apparatus about its axis of symmetry, in contrast to the means described in patents pertaining to angular motion detectors such as in U.S. Pat. No. 3,320,815, dated May 23, 1967, R. E. Bowles, Fluid-Operated Rotational Sensing Device, and U.S. Pat. No. 3,285,073, dated Nov. 15, 1966, W. H. Egli, Coupling Means for Vortex Apparatus, and in contrast to the means shown in patents pertaining to fluid properties and motion detectors such as U.S. Pat. No. 3,580,087, dated May 25, 1971, R. L. Sampson, Fluid Actuated Instrument Sensitive to Density, Temperature or Linear Acceleration.

It should also be noted that the apparatus described with reference to FIGS. 12 and 13 does not incorporate any means of inducing angular velocity or swirl within the fluid passage 116, when the apparatus is stationary where such means might be comprised of tangential nozzles connected to a pressurized fluid source such as in U.S. Pat. No. 3,447,383, dated June 3, 1969, F. J. Camarata, Twin Vortex Angular Rate Sensor, FIG. 3, or might be comprised of circumferential non-radially oriented blades such as in U.S. Pat. No. 3,436,969, dated Apr. 8, 1969, E. R. Phillips, Fluid Vortex Spin Sensor.

In FIGS. 14 and 15, similar parts to those shown in FIGS. 12 and 13 are designated by the same reference numerals and the previous description is relied upon to describe them.

FIGS. 14 and 15 illustrate an apparatus similar to that shown in FIGS. 12 and 13 except that it has a plurality of identical fluid passages, two fluid passages 116 and 148 being shown in FIG. 15 but more than two fluid passages may be used. Both of the fluid passages 116 and 148 receive fluid from the inlet cavity 112 and deliver fluid to the outlet cavity 118. The fluid inlet cavity 112 forms a substantially unobstructed flow path for fluid to the whole area of the inlet end of each fluid passage normal to the direction for flow of fluid of fluid in the fluid passages 116 and 148, and the fluid outlet cavity forms a substantially unobstructed flow path for the escape of fluid from the whole area of the outlet end of each fluid passage normal to the direction for flow of fluid in the fluid passages 116 and 148.

The two fluid passages 116 and 148, are defined by the top and bottom rings spacers 126 and 128, and centre ring spacer 150. The ring spacers 126 and 128 are rigidly located relative to the disc plates 122 and 124 respectively by screws 136. The center ring spacer 150 is comprised of a central annular disc 149 and a coaxial outer annular ring 154 connected together by a number of thin radial spokes 151, four such spokes 151 being shown in FIG. 14. The disc plates 122 and 124, two outer casing rings 152 and 153, and the outer annular ring 154 of center ring spacer 150, are rigidly located and clamped relative to each other by means of screws 138 so as to position the ring spacer 150 equidistance between the ring spacers 126 and 128 without singificantly obstructing the flow of fluid to the fluid passages 116 and 148.

The two total pressure probes 140 and 142 are located in the fluid passage 116, preferably adjacent to the inlet and outlet respectively, of the fluid passage 116.

In operation the embodiment shown in FIGS. 14 and 15 functions in the same manner as the embodiment shown in FIGS. 12 and 13, except that the additional fluid passage 148 allows the apparatus to pass a greater volume of fluid for a given period of time.

In FIGS. 16 and 17, similar parts to those shown in FIGS. 12 and 13 are designated by the same reference numerals and the previous description is relied upon to describe them.

FIGS. 16 and 17 illustrate an apparatus similar to that shown in FIGS. 14 and 15 except that it has two sets of substantially constant width radially extending shims 155 to 160, one set between the ring spacers 126 and 150, and the other set between the ring spacers 150 and 128, which divide each of the fluid passages 116 and 148 into six separate but similar radial flow passages, each of which receives fluid from the inlet cavity 112 and deliver fluid to the outlet cavity 118. The radially extending shims 155 to 160 preferably extend over a substantial radial length of the fluid passages 116 and 148 as shown in FIG. 14. The disc plates 122 and 124, the ring spacers 126, 128 and 150 and both sets of the shims 155 to 160 are rigidly located and clamped relative to each other by means of screws 161, and if necessary, dowel pins, which preferably pass through holes in shims 155 to 160, so as to define the fluid passages 116 and 148, while the outer ring 130 and disc plates 122 and 124 are rigidly located relative to each other by means of the screws 138. The two total pressure probes 140 and 142 are located in the fluid passage 116, preferably adjacent to the inlet and outlet respectively, of the fluid passage 116.

In operation the embodiment shown in FIGS. 16 and 17 functions in the same manner as the embodiments shown in FIGS. 12 and 13 and in FIGS. 14 and 15, except that the additional fluid passage 148 allows the apparatus shown in FIGS. 14 and 15 and in FIGS. 16 and 17 to pass a greater volume of fluid for a given period of time. It will be appreciated that for the embodiment shown in FIGS. 16 and 17 the mean breadth is the sum of the mean arc lengths of each sector of the fluid passage 116 between the radially extending shims 155 to 160 at any given radius from the axis of symmetry.

FIG. 18 illustrates an apparatus similar to that shown in FIGS. 14 and 15 and in FIGS. 16 and 17 except that is has a fluid inlet cavity 162 which is coaxial with the fluid outlet cavity 164, such that the apparatus is symmetrical about a central axis XX. The particular apparatus shown comprises a top disc plate 166, bottom disc plate 168, ring spacers 170 and 172, and two sets of radially extending shims 174 and 176 which define two fluid passage 178 and 180 containing two total pressure probes similar to probes 140 and 142 shown in FIGS. 15 and 17 but which for the purposes of clarity, are not shown in FIG. 18. A conical inlet passage 182 extending between an inlet pipe 184 and the fluid inlet cavity 162 is defined by a conical center body 188, and a conical outer shell 190. It will be evident from FIG. 18 that numerous other inlet and outlet pipe configurations may be incorporated in the apparatus in conjunction with either a single fluid passage 116 as shown in FIG. 13 or a plurality of fluid passages such as fluid passages 116 and 148 as shown in FIGS. 15 and 17.

It will be appreciated that with an apparatus such as shown in FIGS. 15, 17 or 18 or with an apparatus similar to that shown in FIG. 15, 17 or 18 but having more than two fluid passages, any suitable configuration of total pressure probes including that shown in FIGS. 7 and 8 could be radially located at spaced positions in at least one of the fluid passages because the radial distribution of total pressure within all of the fluid passages is the same.

It will also be appreciated that in the multiple fluid passage embodiments of the apparatus as shown in FIGS. 16, 17 and 18, the shims designated 155 to 160 in FIG. 16, could have profiles in plan view differing from that illustrated for purposes of defining a particular fluid passage area dependency upon fluid passage radius as measured from the center of the outlet cavity 118, as may be required in specific applications.

It is particularly useful in practice to combine the individual constant thickness radially oriented shims within any given fluid passage such as shims 155 to 160 shown in FIG. 16 into a single constant thickness shim with a profile in plan view such as that shown in FIG. 19. In FIG. 19 there is shown a shim 191 having a number of identical fingers 192 projecting radially inwards from a circumferential ring 194 where the fingers may have any profile in plan view that is required for a specific application of the apparatus, provided that the fluid passages 196, so defined, continuously reduce in cross-sectional area in the direction of flow of fluid therein.

It will be appreciated that in such an embodiment of the apparatus where profiled shims define the fluid passages, it is within the scope of the present invention that the shim profile could be such that the fluid passages so defined continuously reduces in cross-sectional area in the direction of flow of fluid therein when the fluid flow within the said passages is in a radially outward rather than inward direction, as previously described.

In FIG. 20, similar parts to those shown in FIGS. 17 and 19 are designated by the same reference numerals and the previous description is relied upon to describe them. A cross-sectional view through the circumferential ring 194 and between the fingers 192 of two shims 191, as described with reference to FIG. 19, is shown in part in FIG. 20 where the shims 191 are rigidly located relative to and clamped between components which define two fluid passages 116 and 148 by means of screws 198, which preferably pass through holes 200 in the fingers 192 of each shim 191 as shown in FIG. 19. In FIG. 20, the inner radius of the circumferential ring portion 194 of each profiled shim 191 exceeds the outer radius of the ring spacers 126, 128 and 150 which together define the fluid passages 116 and 148 so as to form substantially unobstructed flow passages from the inlet cavity 112 to the fluid passages 116 and 148 as shown by the fluid flow directional arrows.

It will be appreciated that the single fluid passage configuration such as fluid passage 116 shown in FIGS. 12 and 13, may also incorporate a shim 191 having the configuration shown in FIG. 19, or any plan view variation thereof as required for the purposes of defining suitable fluid flow passage geometries.

It will be appreciated that the modes of operation as described with reference to apparatus shown in FIGS. 2 and 3, FIG. 6, and FIGS. 10 and 11, incorporating what may be considered as segmetrical radial flow and a total pressure measurement means will be directly applicable to the apparatus shown in FIGS. 12 and 13, FIGS. 14 and 15, FIGS. 16 and 17 and FIG. 18, incorporating what may be considered as axisymmetrical radial inflow and a total pressure measurement means.

It will also be appreciated that the modes of operation as described with reference to the apparatus shown in FIGS. 4 and 5, FIG. 6, and FIGS. 10 and 11 incorporating what may be considered as segmented, radial flow but with the total pressure probes replaced by static pressure taps, such as shown in FIG. 9, will be directly applicable to the apparatus shown in FIGS. 12 and 13, FIGS. 14 and 15, FIGS. 16 and 17, and FIG. 18, incorporating what may be considered as axisymmetrical radial inflow provided that the total pressure probes defined for such apparatus are replaced by static pressure taps. It will be further appreciated that such static pressure taps located within the so-called axisymmetric fluid passages of apparatus similar to that shown in FIGS. 12 and 13, FIGS. 14 and 15, FIGS. 16 and 17 and FIG. 18, could be relocated either upstream or downstream of the fluid passage provided that any flow static pressure variations between the original and the relocated pressure tap positions are not significant relative to the static pressure differential along the fluid passage for any particular mode of operation of the apparatus.

It should be noted that the apparatus described with reference to FIGS. 14, 15, 16, 17 and 18, is a fluid flow rate or viscous characteristics measuring device using fluid pressure detection means but which could be located downstream of the fluid passage which is not sensitive to the angular velocity or vorticity of the flow in contrast with the flow angular velocity sensing means downstream of the viscous coupling device shown in U.S. Pat. No. 3,285,073, dated Nov. 15, 1966, W. H. Egli, Coupling Means for Vortex Apparatus. Furthermore, the apparatus described with reference to FIGS. 14, 15, 16, 17 and 18 is a fluid flow rate or viscous characteristic measuring device using a fluid pressure detection means having pressure probes located either within or upstream of the thin fluid passage in contrast with the absence of any fluid detections means either within or upstream of the annular discs shown in U.S. Pat. No. 3,285,073, dated Nov. 15, 1966, W. H. Egli, Coupling Means for Vortex Apparatus.

Yet a further embodiment of the present invention is shown in part in FIG. 21, where individual radial shims, one of which is shown and is designated 202, are radially oriented between fluid passage defining ring spacers 204 and 206, which may be spacers 126 and 128 shown in FIGS. 13. Each shim 202 is bent or contoured in cross-section and is deflected between the spacers 204 and 206. Shims such as shim 202 allow adjustment of the fluid passage mean width between the top spacer 204 and bottom spacer 206 between a limit of the thickness of the shim 202, when fully flattened between the spacers 204 and 206, and a limit of maximum spacing between the spacers 204 and 206 such that the shim 202 remains in sealing contact with both of the spacers 204 and 206.

In FIG. 22 similar parts to those shown in FIGS. 12 and 13 are designated by the same reference numerals and the previous description is relied upon to describe them.

In FIG. 22 an annular top spacer 208 and an annular bottom spacer 210, are tapered to reduce in thickness towards their center such that they define an annular axisymmetrical fluid passage 212 which increases in width towards the fluid outlet cavity 118. By tapering the spacers 208 and 210 in this manner any specific cross-sectional area reduction of the fluid passage 212, in the direction of flow, may be provided for particular applications of the apparatus. While in FIG. 22, both spacers 208 and 210 are shown tapered in thickness, it is also possible to taper only one of the spacers 208 or 210 in this manner to obtain the desired reduction in cross-section of the fluid passage 212. The spacers 208 and 210 are shown reducing in thickness towards the fluid outlet cavity 118 and so, in effect, modify the natural tapering effect on the cross-sectional area, of the fluid passage 212, produced by the flow path being radially inward between two annular spacers 208 and 210. In some instances the desired reduction in cross-sectional area of the fluid passage 212 may be obtained by tapering one or both of the annular spacers 208 and 210 to increase in thickness towards their centers. Although omitted, one or more pressure probes and a corresponding number of fluid pressure transducers, which may be similar to those shown in FIGS. 9 or 13, are necessary for the embodiment shown in FIG. 22 in order to measure the pressure differential in the fluid passage 212.

In FIG. 23, similar parts to those shown in FIGS. 12 and 13 are designated by the same reference numerals and the previous description is relied upon to describe them.

In FIG. 23 there are no pressure probes and/or taps, and the top spacer 216 has flexible member in the form of a flexible, disc-shaped portion 218. The disc-shaped portion 218 is attached to the disc plate 122 and spaced therefrom by a rim portion 219. The deflection of the flexible portion 218 of the spacer 216 is a specific function of the radial static pressure distribution within the fluid passage 220. Thus the differential fluid pressure in the fluid passage 220 is measured by transducers such as strain gauge 221 or air gauge nozzle 223 measuring the strain or deflection respectively of the portion 218 at radially spaced positions and the transducers are, in effect, fluid pressure detectors. This deflection interacts with the static pressure distribution in the fluid passage 220 to alter the mean width of the fluid passage 220 and thus the operational characteristics of the apparatus in a predetermined manner. It will be appreciated that a part or all of the top spacer 216 may consist of a thin sheet of material which may be flat or contoured such as a metal or plastic diaphragm, or it may consist of a sheet of elastic material such as rubber which may be reinforced or stiffened. It will be noted that in FIG. 23 the fluid outlet cavity 118 extends only through the bottom spacer 128 and bottom plate 124, and that a vent 222, which is not essential, is shown in the top plate 122.

The means of detecting the deflection and/or the strain of the flexible portion 218, to provide an indication of the radial static pressure distribution within fluid passage 220 as related to the deflection profile of the portion 218, may comprise resistance wire strain gauges 221 attached to the surface of the flexible portion 218, or air gauges with the nozzles 223 located immediately adjacent to the surface of the flexible wall 218, or any other known means of strain or deflection measurement.

In FIG. 24, similar parts to those shown in FIG. 23 are designated by the same reference numerals and the previous description is relied upon to describe them.

In FIG. 24, a means 224 of deflecting the flexible portion 218 is provided to attain a particular configuration of the fluid passage 220 other than that generated by the radial pressure distribution within the fluid passage 220. The deflection means 224 attached to the flexible portion 218 may be a servo controlled jack, a force or displacement generating device, such as a hydraulic cylinder, electrical solenoid, screw jack, or similar device, or any of a multitude of such devices, as are known to those familiar with the art. Such a force or displacement generating component may be arranged to be responsive to the strain or deflection within the flexible portion 218, as detected by such means described with reference to FIG. 23, by means of feedback (not shown) to the deflection means 224 of suitably conditioned signals derived from the strain or deflection measurements such that the effect of the radial pressure distribution on the deflection of the flexible portion 218 may be amplified or characterized using such feedback control methods as will be known to those familiar with the art. It will be further appreciated that a displacement generating means such as the device 224 may be used to attain specific configuration of the fluid passage 220 by presetting and/or controlling the means 224 or a multiplicity of such means.

It will appreciated that, in any of the embodiments of the invention described herein, it is within the scope of the present invention to place more than one total pressure probe or static pressure tap at any given lengthwise or radial location within the fluid flow passage so as to provide for, say, an alternative measurement at that radial location or a system whereby a plurality of pressure measurements at that radial location may be averaged.

It will be further appreciated that the various embodiments, according to the present invention, described herein are not limited in physical size or geometric scale within the constraints of practical fabrication accuracy considerations and of laminar flow maintenance within the fluid flow passages.

It will be further appreciated that two or more so-called segmetrical configurations or so-called axisymmetrical configurations of the apparatus described herein, with either single or multiple fluid passages, can be combined while maintaining separate fluid sources and apparatus inlet cavities such that the characteristics of two or more fluids may be simultaneously detected where one or more of the fluids may be considered a reference fluid.

We claim:
1. Apparatus for measuring the flow rate and/or the viscous characteristics of a fluid, comprising:
   a. a casing having a fluid passage, a fluid inlet cavity for connection to a source of pressurized fluid and forming a substantially unobstructed flow path for fluid to the whole area of an inlet end of the fluid passage, normal to the direction for flow of fluid in the fluid passage, and a fluid outlet cavity for the escape of fluid from the casing and forming a sub stantially unobstructed flow path for fluid from substantially the whole area of an outlet end of the fluid passage, normal to the direction for flow of fluid in the fluid passage, b. fluid pressure detecting means in the casing for detecting a fluid pressure differential between spaced positions in the fluid passage in the direction for flow of fluid therein, and c. fluid pressure indicating means, connected to the fluid pressure detecting means, from which the fluid pressure differential in the fluid passage can be deduced, and wherein, d. the ratio of the mean breadth to the mean width of the fluid passare area, normal to the direction for flow of fluid therein, is at least ten to one for at least the portion of the fluid passage which extends between the said spaced positions, e. the area of the fluid passage, normal to the direction for flow of fluid in the fluid passage, and for at least the portion of the fluid passage which extends between the said spaced positions, continuously reduces in size in the direction for flow of the fluid such that laminar flow will be maintained of the fluid flowing in the passage, and such that when using substantially pure water at 70°F as a standard, the static pressure differential at said spaced locations is dependant upon the mass flow rate G of the substantially pure water through the fluid passage and satisfies the relationship in consistent units:

$$\Delta p = K_1 (G)^2 + K_2 (G),$$ and ii. the total pressure differential at said spaced locations is linearly dependant upon the mass flow rate G of the substantially pure water in the fluid passage, and the above pressure differential relationships for static and total pressure differential ($\Delta p$ and $\Delta P$ respectively) are over a range of flow rates for the substantially pure water for which the difference between the maximum Reynolds numbers in the fluid passage between the said spaced positions therein is within the range 0 and 8000, where the Reynolds number $R_e$ is defined, in consistent units, by:

$R_e = h\rho U/\mu$, where $h$ = the mean width of the fluid passage at the position between the said spaced positions for which the Reynolds number is a maximum, $\rho$ = the fluid density of the substantially pure water, $U$ = the means velocity of the substantially pure water at the position between the said spaced positions for which the Reynolds number is a maximum, and $\mu$ = the absolute viscosity of the substantially pure water, and where in the case of static pressure differential the ratio $K_1/K_2$ is greater than 0.01, where $K_1$ and $K_2$ are constants for a given fluid passage geometry and are determined from the relationships:

$$K_2 = \frac{\Delta P_1 - \Delta P_2 \left(\frac{G_1^2}{G_2^2}\right)}{G_1 - \frac{(G_1)^2}{G_2}},$$

and $$K_1 = \frac{\Delta P_1 - K_2 (G_1)}{(G_1)^2} = \frac{\Delta P_2 - K_2 (G_2)}{(G_2)^2},$$

where $\Delta p_1$ = static pressure differential between the said spaced positions when the maximum Reynolds number in the fluid passage between the said spaced positions is 8000, $G_1$ = the fluid mass flow rate of the substantially pure water through the fluid passage when the maximum Reynolds number in the fluid passage between the said spaced positions is 8000, $\Delta p_2$ = static pressure differential between the said spaced positions when the maximum Reynolds number in the fluid passage between the said spaced positions is 3500, $G_2$ = the fluid mass flow rate of the substantially pure water through the fluid passage when the maximum Reynolds number in the fluid passage between the said spaced positions is 3500, so that f. the fluid characteristic to be measured is related to the pressure differential, indicated by the fluid pressure differential indicating means, and is deducible therefrom in a consistent manner for different fluids.

2. Apparatus according to claim 1, wherein the fluid pressure means comprises two static pressure taps in the casing and each is in communication with one of the said spaced positions within the fluid passage.

3. Apparatus according to claim 1, wherein the fluid pressure detecting means comprises one static pressure tap and one total pressure probe and each is in communication with one of the said spaced positions.

4. Apparatus according to claim 1, wherein the fluid pressure detecting means comprises one static pressure tap and one total pressure probe each located at one of the said spaced positions.

5. Apparatus according to claim 1, wherein the fluid pressure detecting means comprises two detectors in the form of a static pressure tap and a total pressure probe, and one detector is in communication with one of the said spaced positions and the other detector is located at the other of the said spaced positions.

6. Apparatus according to claim 1, wherein one of the said spaced positions is located between the inlet and the outlet of the fluid passage at a position such that the detected pressure differential is measurably sensitive to variations of fluid viscosity, and the fluid detection means comprises static pressure taps.

7. Apparatus according to claim 1, wherein the fluid pressure detecting means comprises at least three static pressure taps at spaced locations between the said spaced positions, and the fluid pressure indicating means comprises a plurality of pressure measuring instruments each connected to one of the static pressure taps so that the static pressure distribution between the said spaced positions can be deduced.

8. Apparatus according to claim 1, wherein the fluid pressure detecting means comprises two total pressure probes in the casing and located at the said spaced positions.

9. Apparatus according to claim 1, wherein one of the said spaced positions is located between the inlet and the outlet of the fluid passage such that the detected pressure differential is measurably sensitive to variations of fluid viscosity and the fluid detection means comprises total pressure probes.

10. Apparatus according to claim 1, wherein the fluid pressure detecting means comprises at least three total pressure probes at spaced locations between the said spaced positions, and the fluid pressure indicating means comprises a plurality of pressure measuring instruments each connected to one of the total pressure probes so that the total pressure distribution between the said spaced positions can be deduced.

11. Apparatus according to claim 1, wherein the casing is a cylindrical casing containing an outer, annular shaped fluid inlet cavity, an intemediate, annular shaped fluid passage for radial inward flow of fluid therethrough, and an inner, fluid outlet cavity, and wherein the outer annular shaped fluid inlet cavity forms the substantially unobstructed flow path to the whole outer periphery of the intermediate annular shaped fluid passage and the inner, fluid outlet cavity forms the substantially unobstructed flow path from the whole inner periphery of the intermediate, annular shaped fluid passage for the escape of fluid from the casing, and the fluid pressure detecting means in the casing is for detecting a fluid pressure differential between radially spaced positions in the fluid passage.

12. Apparatus according to claim 11, which includes a conical center body attached to one side of the cylindrical casing, and a conical outer shell surrounding and spaced from the conical center body, the conical outer shell being attached to the casing so that the space between the conical center body and the conical outer shell is a conical inlet passage extending around the whole of the fluid inlet cavity, for delivering the pressurized fluid thereto from the pressurized fluid source.

13. Apparatus according to claim 1, which includes a flexible member in the casing forming one wall of the fluid passage and attached to the casing around the edge of the flexible member to space a portion of the said member from the casing, and deflection transducers forming the fluid pressure detecting means are attached to the flexible member to detect the fluid pressure differential by measuring deflections of the flexible member.

14. Apparatus according to claim 1, which includes a flexible member in the casing and attached thereto around the edge of the flexible member to space a portion of the said member from the casing and deflecting means for deflecting the flexible member to adjust the distance between the walls of the passage to define the said area of the fluid passage.

15. Apparatus for measuring the flow rate and/or the viscous characteristics of a fluid, comprising:
   a. a casing having a plurality of substantially identical fluid passages, a fluid inlet cavity for connection to a source of pressurized fluid and forming a substantially unobstructed flow path for fluid to the whole area of the inlet end of each fluid passage, normal to the direction for flow of fluid in the fluid passage, and a fluid outlet cavity for the escape of fluid from the casing and forming a substantially unobstructed flow path for each fluid passage,
   b. fluid pressure detecting means in the casing for detecting a fluid pressure differential between spaced positions in at least one of the fluid passages in the direction for flow of fluid therein, and
   c. fluid pressure indicating means, connected to the fluid pressure detecting means, from which the fluid pressure differential in at least the said one of the fluid passages can be deduced, and wherein,
   d. the ratio of the mean breadth to the mean width of each fluid passage area, normal to the direction for flow of fluid therein, is at least ten to one for at least the portion of the fluid passages which extends between the said spaced positions,
   e. the area of each fluid passage, normal to the direction for flow of fluid in the fluid passage, and for at least the same portion of each fluid passage as that which extends between the said positions, continuously reduces in size in the direction for flow of the fluid such that laminar flow will be maintained of the fluid flowing in each fluid passage, and each fluid passage is such that when using substantially pure water at 70°F as a standard, and
   i. the static pressure differential a at said spaced locations is dependant upon the mass flow rate G of the substantially pure water through the fluid passage and satisifies the relationship in consistent units:

$$\Delta p = K_1 (G)^2 + K_2 (G),$$

and
   ii. the total pressure differential at said spaced locations is linearly dependant upon the mass flow rate G of the substantially pure water in the fluid passage, and the above pressure differential relationships for static and total pressure differential ($\Delta p$ and $\Delta P$ respectively) are over a range of flow rates for the substantially pure water for which the difference between the maximum Reynolds numbers in the fluid passage between the said spaced positions therein is within the range 0 and 8000, where the Reynolds number $R_e$ is defined, in consistent units, by:

$$R_e = h\rho U/\mu,$$

where
   $h$ = the mean width of the fluid passage at the position between the said spaced positions for which the Reynolds number is a maximum,
   $\rho$ = the fluid density of the substantially pure water,
   $U$ = the mean velocity of the substantially pure water at the position between the said spaced positions for which the Reynolds number is a maximum,
   $\mu$ = the absolute viscosity of the substantially pure water, and where in the case of static pressure differential the ratio
   $K_1/K_2$ is greater than 0.01, and $K_1$ and $K_2$ are constants for given substantially identical fluid passage geometries and are determined from the relationships:

$$K_2 = \frac{\Delta P_1 - \Delta P_2 \left(\frac{G_1^2}{G_2}\right)}{G_1 - \frac{(G_1)^2}{G_2}},$$

and $$K_1 = \frac{\Delta P_1 - K_2 (G_1)}{(G_1)^2} \quad \frac{\Delta P_2 - K_2 (G_2)}{(G_2)^2},$$

where
   $\Delta p_1$ = static pressure differential between the said spaced positions when the maximum Reynolds number in the fluid passage between the said spaced positions is 8000, $G_1$ = the fluid mass flow rate of the substantially pure water through the fluid passage when the maximum Reynolds number in the fluid passage between the said spaced positions is 8000, $\Delta p_2$ = static pressure differential between the said spaced positions when the maximum Reynolds number in the fluid passage between the said spaced positions is 3500, $G_2$ = the fluid mass flow rate of the substantially pure water through the fluid passage when the maximum Reynolds number in the fluid passage between the said spaced positions is 3500, so that f. the characteristic to be measured is related to the pressure differential, indicated by the fluid pressure differential indicating means, and is deducible therefrom in a consistent manner for different fluids.

16. Apparatus according to claim 15, wherein the fluid pressure detecting means comprises two static pressure taps in the casing and each is in communication with one of the said spaced positions in a fluid passage.

17. Apparatus according to claim 15, wherein the said spaced positions are in one fluid passage, and the two static pressure taps are located at the spaced positions.

18. Apparatus according to claim 15, wherein the said spaced positions are in different fluid passages, and the two static pressure taps are located at the spaced positions.

19. Apparatus according to claim 15, wherein the fluid pressure detecting means comprises two static pressure taps, one of which is in communication with one of the said spaced positions and the other of which is located at the other spaced position.

20. Apparatus according to claim 15, wherein the fluid pressure detecting means comprises one static pressure tap and one total pressure probe and each is in communication with one of the said spaced positions.

21. Apparatus according to claim 15, wherein the said spaced positions are in one fluid passage, and the fluid pressure detecting means comprises one static pressure tap and one total pressure probe each located at one of the said spaced positions.

22. Apparatus according to claim 15, wherein the said spaced positions are in different fluid passages, and the fluid pressure detecting means comprises one static pressure tap and one total pressure probe each located at one of the said spaced positions.

23. Apparatus according to claim 15, wherein the fluid pressure detecting means comprises two detectors in the form of a static pressure tap and a total pressue probe, and one detector is in communication with one of the said spaced positions and the other detector is located at the other of the said spaced positions.

24. Apparatus according to claim 15, wherein one of the said spaced positions is located between the inlet and the outlet of one of the fluid passages at a position such that the detected pressure differential is measurably sensitive to variations of fluid viscosity, and the fluid detection means comprises static pressure taps.

25. Apparatus according to claim 15, wherein the fluid pressure detecting means comprises at least three static pressure taps each in a fluid passage and at spaced locations from each other between the said spaced positions, and the fluid pressure indicating means comprises a plurality of pressure measuring instruments each connected to one of the static pressure taps so that the static pressure distribution between the said spaced positions can be deduced.

26. Apparatus according to claim 15, wherein the said spaced positions are in one fluid passage, and the fluid pressure detecting means comprises two total pressure probes in the casing located the said spaced positions.

27. Apparatus according to claim 15, wherein the said spaced positions are in different fluid passages, and the fluid pressure detecting means comprises two total pressure probes in the casing and located at the said spaced positions.

28. Apparatus according to claim 15, wherein the fluid pressure detecting means comprises two total pressure probes in the casing and in communication with each of the said positions.

29. Apparatus according to claim 15, wherein one of the said spaced positions is located between the inlet and the outlet of one of the fluid passage at a position such that the detected pressure differential is measurably sensitive to variations of fluid viscosity and the fluid detection means comprises total pressure probes.

30. Apparatus according to claim 15, wherein the fluid pressure detecting means comprises at least three total pressure probes each in one of the fluid passages and at spaced locations from each other between the said spaced positions, and the fluid pressure indicating means comprises a plurality of pressure measuring instruments each connected to one of the total pressure probes so that the total pressure distribution between the said spaced positions can be deduced.

31. Apparatus according to claim 15, wherein the casing is a cylindrical casing containing an outer, annular shaped fluid inlet cavity, a plurality of similar, coaxial, annular intermediate, fluid passages, each for substantially radial inward flow of fluid therethrough, and an inner, fluid outlet cavity, and wherein the outer annular shaped fluid inlet cavity forms a substantially unobstructed flow path to the whole outer periphery of each intermediate annular shaped fluid passage, and the inner fluid outlet cavity forms a substantially unobstructed flow path from the whole inner, periphery of each intermediate, annular shaped fluid passage for the escape of fluid from the casing, and the fluid pressure detecting means is for detecting a fluid pressure differential at two radially spaced positions each in one of the fluid passages.

32. Apparatus according to claim 31, which includes a conical center body attached to one side of the cylindrical casing, and a conical outer shell surrounding and spaced from the conical center body, the conical outer shell being attached to the casing so that the space between the conical center body and the conical outer shell is a conical inlet passage extending around the whole of the fluid inlet cavity, for delivering pressurized fluid thereto from the pressurized fluid source.

33. Apparatus according to claim 15, wherein the casing is a cylindrical casing containing an outer, annular shaped fluid inlet cavity, an annular, intermediate cavity, and an inner, fluid outlet cavity, and a plurality of shims extending radially inwards within the annular, intermediate cavity partition the said annular, intermediate cavity into a plurality of radially extending fluid passages, with the outer annular shaped inlet cavity forming the substantially unobstructed flow path to the whole area of the inlet end of each radial fluid passage, and the inner annular shaped outlet cavity forming a substantially unobstructed flow path from the whole area of the outlet end of each radial fluid passage, and the fluid pressure detecting means is for detecting a fluid pressure differential at two radially spaced positions in at least one of the said fluid passages.

34. Apparatus according to claim 33, which includes at least one disc spacer in the annular cavity, whereby the annular, intermediate cavity is separated into one of a plurality of similar, coaxial, annular, intermediate cavities, each annular, intermediate cavity contains radially extending shims to partition the annular, intermediate cavities into similar, radially extending fluid passages, with all of the fluid passages having a substantially unobstructed flow path thereto from the outer, annular shaped fluid inlet cavity and a substantially unobstructed flow path therefrom to the inner, fluid outlet cavity.

35. Apparatus according to claim 33, wherein each of the shims are similarily contoured in cross-section and are deflected between the walls of the casing to be held in position.

36. Apparatus according to claim 34, wherein each of the shims are similarily contoured in cross-section and are deflected in position in each fluid passage to be thereby held in position by the casing and at least one disc spacer.

37. Apparatus according to claim 33, wherein each shim has an extension which extends radially outwardly into the fluid inlet cavity, and the said shim extensions are joined by a circumferential ring attached to the extension and coaxially positioned in the fluid inlet cavity.

38. Apparatus according to claim 34, wherein each shim has an extension which extends radially outwardly into the fluid inlet cavity, and the said shim extensions extending from each coaxial, annular, intermediate cavity are joined by a circumferential ring attached to the extensions and coaxially positioned in the fluid inlet cavity.

* * * * *